US012774292B2

(12) United States Patent
Wong et al.

(10) Patent No.: US 12,774,292 B2
(45) Date of Patent: Oct. 27, 2026

(54) LMP1 TARGETING LANTHANIDE COMPLEXES AND METHODS OF USE THEREOF

(71) Applicant: BP InnoMed Limited, Hong Kong (CN)

(72) Inventors: Ka-Leung Wong, Hong Kong (CN); Hong Lok Lung, Hong Kong (CN); Ho-Fai Chau, Hong Kong (CN)

(73) Assignee: BP InnoMed Limited, Hong Kong (CN)

( * ) Notice: Subject to any disclaimer, the term of this patent is extended or adjusted under 35 U.S.C. 154(b) by 1130 days.

(21) Appl. No.: 17/807,900

(22) Filed: Jun. 21, 2022

(65) Prior Publication Data

US 2023/0097293 A1 Mar. 30, 2023

Related U.S. Application Data

(60) Provisional application No. 63/202,687, filed on Jun. 21, 2021.

(51) Int. Cl.
*C07F 5/00* (2006.01)
*A61P 35/00* (2006.01)

(52) U.S. Cl.
CPC .............. *C07F 5/003* (2013.01); *A61P 35/00* (2018.01)

(58) Field of Classification Search
None
See application file for complete search history.

(56) References Cited

PUBLICATIONS

Chau (Lanthanide-Based Peptide-Directed Visible/Near-Infrared Imaging and Inhibition of LMP1. JACS. Jun. 20, 2021.). (Year: 2021).*
Chau (Lanthanide-Based Peptide-Directed Visible/Near-Infrared Imaging and Inhibition of LMP1. Supplemental Information. JACS. Jun. 20, 2021.). (Year: 2021).*

* cited by examiner

*Primary Examiner* — Michael G. Hartley
*Assistant Examiner* — Samantha L Mejias
(74) *Attorney, Agent, or Firm* — S&F/WEHRW

(57) ABSTRACT

Polypeptides useful for treating and/or imaging latent membrane protein 1 positive cells, such as cells infected with Epstein-Barr virus and Epstein-Barr virus-associated cancers, pharmaceutical compositions comprising the same, and methods of use thereof.

18 Claims, 18 Drawing Sheets

Specification includes a Sequence Listing.

Table 1

| $LC_{50}/\mu M$ | LCL3 | AFB1 | AG876 | C666-1 | HeLa | MRC5 |
|---|---|---|---|---|---|---|
| **P19C** | >200 | >200 | >200 | >200 | >200 | >200 |
| **P19** | 14.8 ± 0.76 | 13.6 ± 2.33 | 26.4 ± 3.06 | 71.1 ± 4.58 | 94.0 ± 4.15 | 108 ± 0.93 |
| **EuP19** | 12.4 ± 2.07 | 19.1 ± 3.60 | 38.7 ± 5.63 | 66.7 ± 4.48 | 123 ± 5.51 | 111 ± 2.52 |
| **YbP19** | 15.4 ± 1.32 | 16.2 ± 2.76 | 36.5 ± 4.31 | 78.6 ± 1.22 | 127 ± 2.88 | 98.3 ± 3.10 |

FIG. 3 b

| | Quantum Yield (%) | τ ($H_2O$) | τ ($D_2O$) | Q-value [a] |
|---|---|---|---|---|
| **EuP19** | 8.27 | 0.589 ms | 1.76 ms | 1.05 |
| **YbP19** | 0.05 | - | - | - |

[a]q = 1.2 × [k($H_2O$) - k($D_2O$) - 0.25]

LMP1 TARGETING LANTHANIDE COMPLEXES AND METHODS OF USE THEREOF

CROSS-REFERENCE TO RELATED APPLICATIONS

The specification further incorporates by reference the Substitute Sequence Listing submitted herewith via EFS-Web on Oct. 14, 2022. The Substitute Sequence Listing text file, identified as Sequence_Listing_P23297US01, is 5.66K bytes and was created on Oct. 14, 2022. The Substitute Sequence Listing electronically filed Oct. 14, 2022 does not contain new matter.

REFERENCE TO SEQUENCE LISTING

The specification further incorporates by reference the Substitute Sequence Listing submitted herewith via EFS-Web on Sep. 13, 2022. The Substitute Sequence Listing text file, identified as Sequence Listing 034695-000004.txt, is 6K bytes and was created on Sep. 6, 2022. The Substitute Sequence Listing electronically filed Sep. 13, 2022 does not contain new matter.

TECHNICAL FIELD

The present disclosure relates to a lanthanide-based peptide-directed theranostic agent useful for treating and/or imaging latent membrane protein 1 positive cells, such as cells infected with Epstein-Barr virus.

BACKGROUND

Epstein-Barr virus (EBV) belongs to the gamma herpesvirus family, which infects more than 90% of the population worldwide. Despite the widespread condition of EBV, latent infection is developed in most cases. EBV tends to infect B lymphocyte in immunocompetent host, persist in memory B cell pool, and remains asymptomatic with life-long latent infection. During latent infection, only a handful of EBV latent genes are expressed. Latent membrane protein 1 (LMP1) is one of those viral gene products, it is the major transforming protein of EBV and is critical for EBV-induced B-cell transformation in vitro. LMP1 is also important in tumor cell proliferation, immortalization and angiogenesis. The oncogenic functions of LMP1 have been implicated in a variety of EBV-related cancers including Hodgkin's disease, non-Hodgkin lymphoma, nasopharyngeal carcinoma (NPC) and gastric cancer. Taken together with its localization in the cell membrane, LMP1 is considered an attractive therapeutic target in EBV-associated malignancies.

LMP1 is an integral membrane protein which has the molecular weight of 66 kDa. It contains three structural parts: a short 24 amino acid residue cytoplasmic N-terminus, six transmembrane domains (TM1-6) with five short reverse turn in-between, and a long 200 amino acid residue cytoplasmic C-terminus. It functions by mimicking the cell surface receptor CD40 to recruit tumor necrosis factor receptor associated signaling proteins in a ligand-independent manner. This activates several cellular pathways including nuclear factor-κB (NF-κB), mitogen-activated protein kinase and phosphatidylinositol 3-kinase pathways. Induction of transcription of multiple target genes will be resulted once these pathways are activated, leading to cell proliferation, invasion and cell cycle progression. While the cytosolic C-terminus proportion of LMP1 is responsible for intracellular signal transduction which causes nuclear translocation of transcription factors, the transmembrane (TM) domains play a crucial role in signaling initiation at the cell membrane. The TM domains of LMP1 facilitates its aggregation and oligomerization in the lipid raft, causing LMP1 to be constitutively active for cellular signaling. The TM1-2 domains contain the lipid raft targeting signals, and thus are critical to cluster the LMP1 monomers via the association with the lipid raft. These domains are also essential to mediate intermolecular interaction among the LMP1 monomers, which contributes in a large proportion of LMP1-mediated NF-κB activation, whereas other TMs do not have any role in signaling transduction. Mutation in the TM1 domain of LMP1 also results in reduction in protein stability and lipid raft aggregation. Within TM1, its amino acid residues $FWLY_{38-41}$ (Amino acids 38-41, SEQ ID NO:4) play a crucial role in NF-κB activation, as the activation pathway is impaired upon $FWLY_{38-41}$ (Amino acids 38-41, SEQ ID NO:4) mutation, the intermolecular interaction between the TM domains is abrogated, and the association between the lipid raft and other signaling proteins is also weakened.

There thus exists a need for improved imaging and/or therapeutic agents that are capable of selectively targeting LMP1 positive cells, such as EBV infected cells and EBV-associated malignancies.

SUMMARY

The present disclosure relates to lanthanide-based peptide-directed bioprobes, exemplified by LnP19 (Ln=Eu or Yb), useful as dual-functional probes for the EBV oncoprotein LMP1. The peptide P19 (Pra-KAhx-K-LDLALK-FWLY-K-IVMSDKW-K-RrRK, SEQ ID NO:2) is designed to selectively bind to LMP1 by mimicking its TM1 region during oligomerization in lipid rafts while signal transduction is significantly suppressed. Immunofluorescence imaging and Western blotting results reveal that P19 can effectively inactivate the oncogenic cellular pathway nuclear factor κB (NF-κB) and contribute to a selective cytotoxic effect on LMP1-positive cells. By conjugation with cyclen-based europium (III) and ytterbium (III) complexes, EuP19 and YbP19 were constructed to offer visible and near-infrared LMP1-targeted imaging and cancer monitoring. In addition to the ability to target and inhibit LMP1 and to selective inhibit LMP1-positive cells, the selective growth inhibition towards LMP1-positive tumor by LnP19 is also demonstrated.

In a first aspect, provided herein is a polypeptide comprising SEQ ID NO:1, wherein the N-terminus of the residue at position one of SEQ ID NO:1 is covalently bonded to a moiety represented by the structure: X—Y—Z, wherein X is a click residue or a click cycloadduct, Y is a lysine residue; and Z is a linker, and each of the residues at positions one, twelve, and twenty of SEQ ID NO:1 is independently a water-soluble residue selected from the group consisting of lysine, arginine, histidine, aspartic acid, and glutamic acid, wherein the click residue is a moiety of Formula 1:

1

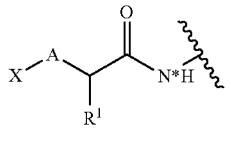

wherein N* is the n-terminal nitrogen of the lysine residue;

A is $(CR^2{}_2)_m$, aryl, or —$CH_2$-aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl;

X is —$N_3$, —C≡CH, —$OCH_2C$≡CH, —$NHCH_2C$≡CH, —NH(C═O)$OCH_2C$≡CH, —NH(C═O)$NHCH_2C$≡CH, —O(C═O)$OCH_2C$≡CH, or —O(C═O)$NHCH_2C$≡CH; or X is a moiety selected from the group consisting of:

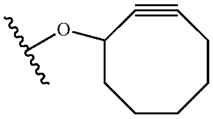

and

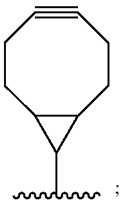

;

m is a whole number selected from 0-10;

the click cycloadduct is a moiety of Formula 3:

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl; and m is a whole number selected from 0-10; and the linker is a moiety of Formula 2:

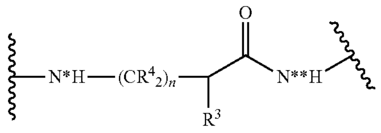

2 wherein N* is covalently bonded to the c-terminal carbon of lysine residue and N** is covalently bonded to the residue at position one of SEQ ID NO:1;

$R^3$ is hydrogen or amino;

$R^4$ for each instance is independently hydrogen, alkyl, cycloalkyl, or aryl; or two instances of $R^4$ and the carbons to which they are bonded form a 3-6 membered cycloalkyl; and n is a whole selected from 0-10.

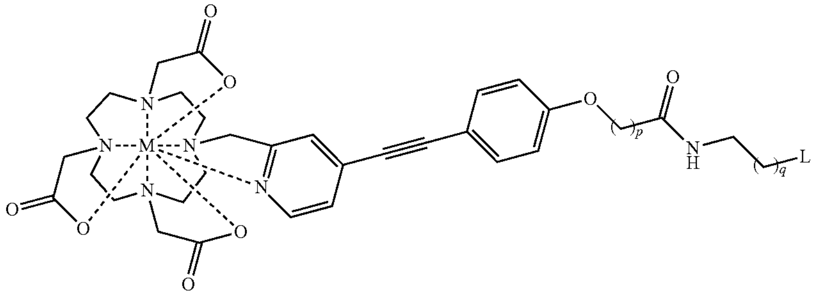

3 wherein M is a lanthanide or is absent;

p is a whole number selected from 0-6;

q is a whole number selected from 0-6; and

L is a moiety selected from the group consisting of:

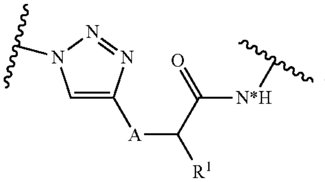

and

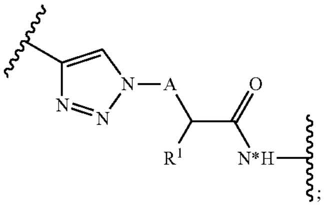

;

wherein N* is the n-terminal nitrogen of the lysine residue;

A is $(CR^2{}_2)_m$, aryl, or —$CH_2$-aryl;

In certain embodiments, the click residue is a moiety of Formula 1:

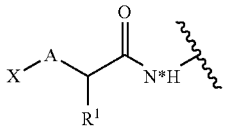

1 wherein N* is the n-terminal nitrogen of the lysine residue;

A is $(CR^2{}_2)_m$, aryl, or —$CH_2$-aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl;

X is —$N_3$, —C≡CH, —$OCH_2C$≡CH, or —$NHCH_2C$≡CH; and m is a whole number selected from 0-10.

In certain embodiments, the click residue is selected from the group consisting of:

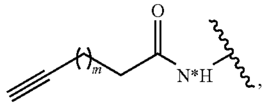, 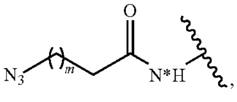,

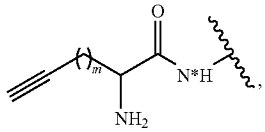, 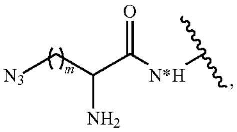,

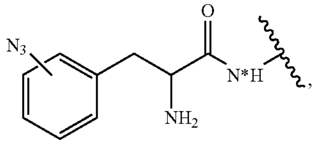,

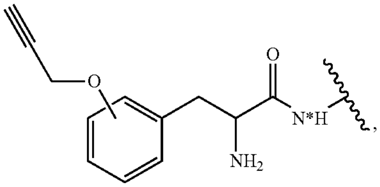,

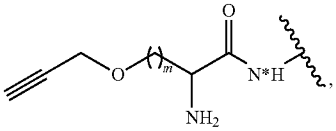, and

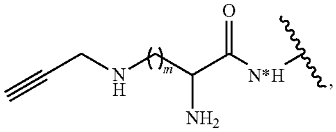, wherein m is a whole number selected from 1-4.

In certain embodiments, the click residue is selected from the group consisting of:

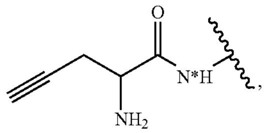, 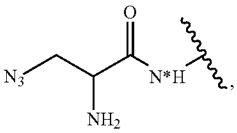,

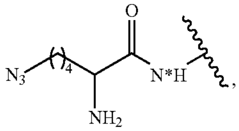,

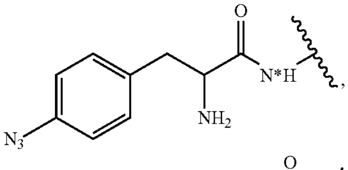,

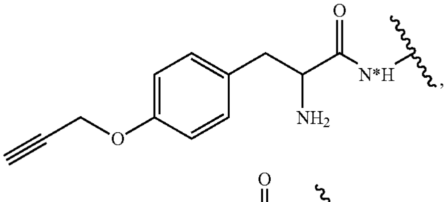,

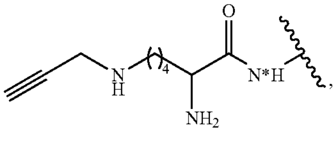, and

-continued

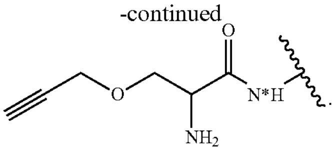.

In certain embodiments, the linker is a moiety selected from the group consisting of:

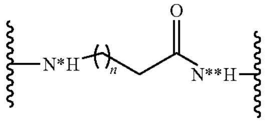 and

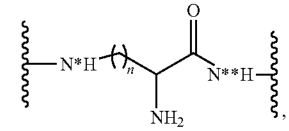, wherein n is a whole number selected from 0-8.

In certain embodiments, the linker is a moiety having the structure:

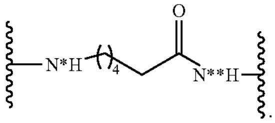.

In certain embodiments, each of the water-soluble residues is independently selected from the group consisting of lysine, arginine, and histidine.

In certain embodiments, each of the water-soluble residues is lysine.

In certain embodiments, the polypeptide comprises SEQ ID NO:2.

In certain embodiments, p is 1 or 2; and q is 1, 2, or 3.

In certain embodiments, L is a moiety selected from the group consisting of:

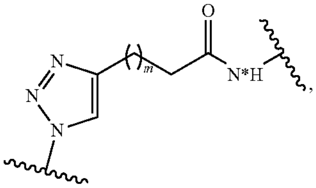,

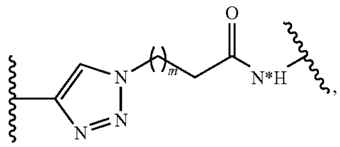,

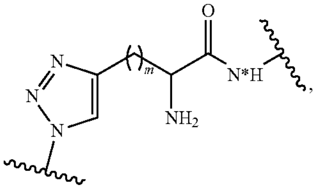,

-continued
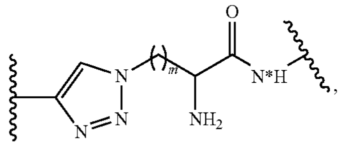
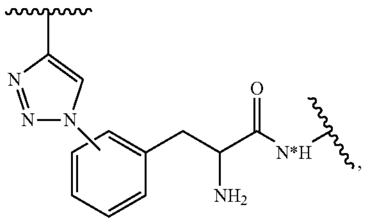
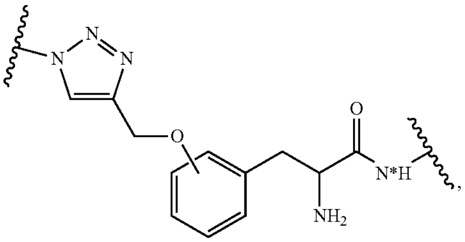
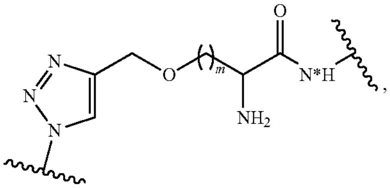
and
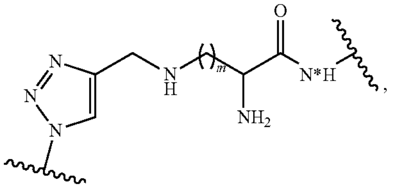
wherein m is a whole number selected from 1-4.
In certain embodiments, L is a moiety selected from the group consisting of:
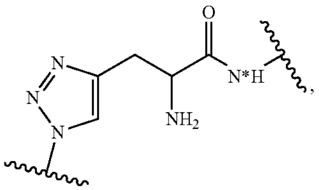
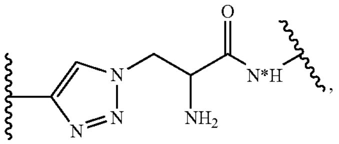
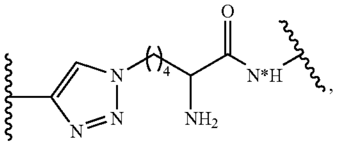
-continued
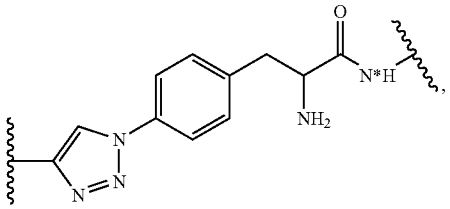
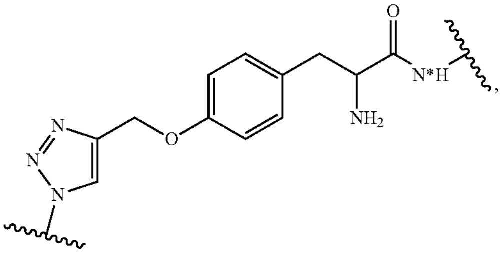
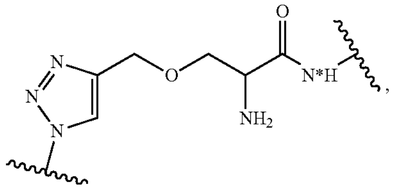
and
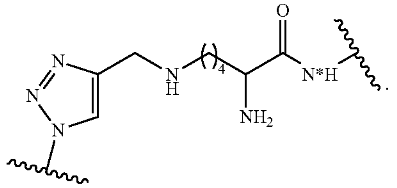
In certain embodiments, L is a moiety selected from the group consisting of:
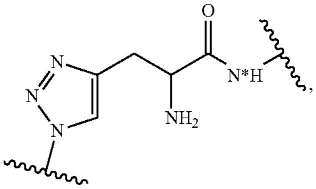
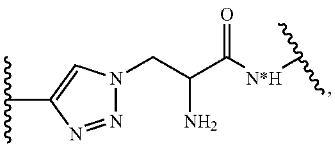
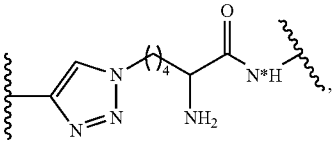
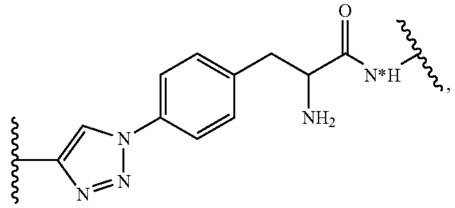

-continued

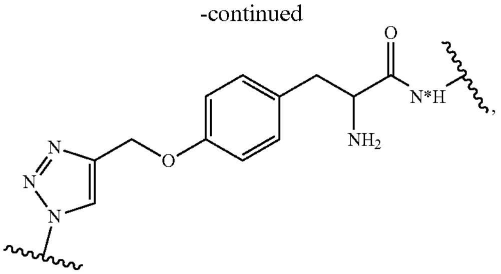,

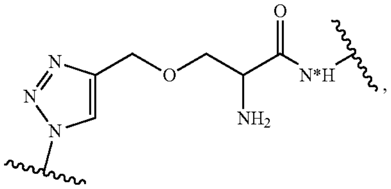, and

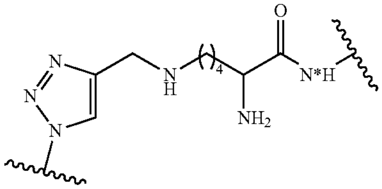;

and the linker is a moiety having the structure:

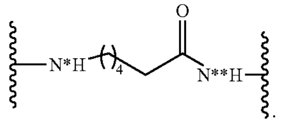.

In certain embodiments, each of the water-soluble residues is independently selected from the group consisting of lysine, arginine, and histidine.

In certain embodiments, L is a moiety having the structure:

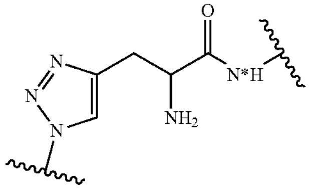

the linker is a moiety having the structure:

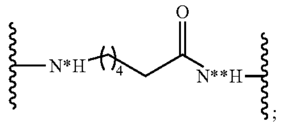;

each of the water-soluble residues is lysine.

In certain embodiments, p is 1; and q is 1.

In a second aspect, provided herein is a pharmaceutical composition comprising the polypeptide of the first aspect and at least one pharmaceutically acceptable excipient.

In a third aspect, provided herein is a method of treating an Epstein-Barr virus infection in a subject in need thereof comprising administering a therapeutically effective amount of a polypeptide of the first aspect to the subject.

In a fourth aspect, provided herein is a method of treating cancer in a subject in need thereof comprising administering a therapeutically effective amount of a polypeptide of the first aspect to the subject, wherein the cancer is an Epstein-Barr virus-associated cancer.

In certain embodiments, the Epstein-Barr virus-associated cancer is selected from the group consisting of Burkitt's lymphoma, non-Hodgkin's lymphoma, Hodgkin's disease, T-cell lymphoma, B-cell lymphoma, B-lymphoproliferative disease, natural killer-cell lymphoma, transplant-associated lymphoproliferative disorders, nasopharyngeal carcinoma, gastric adenocarcinoma, parotid carcinoma, plasmablastic lymphoma, primary effusion lymphoma, and leiomyosarcoma.

In a fifth aspect, provided herein is a method of imaging a cell suspected of being latent membrane protein 1 positive, the method comprising contacting the cell with a polypeptide described herein; irradiating the cell with electromagnetic radiation having a wavelength within the activation wavelength of the polypeptide; and imaging the fluorescence of the polypeptide.

BRIEF DESCRIPTION OF THE DRAWINGS

The above and other objects and features of the present disclosure will become apparent from the following description of the disclosure, when taken in conjunction with the accompanying drawings.

FIG. 3 depicts Table 1 showing a summary of the $LC_{50}$ values of P19C, P19, EuP19 and YbP19 in different cell lines, data are expressed as mean±SD.

Confocal live imaging of NF-κB reporter LCL3 cells with 10 μM EuP19 incubation ($\lambda_{ex}$=491 nm; scale bar: 100 μm).

Figure 6:
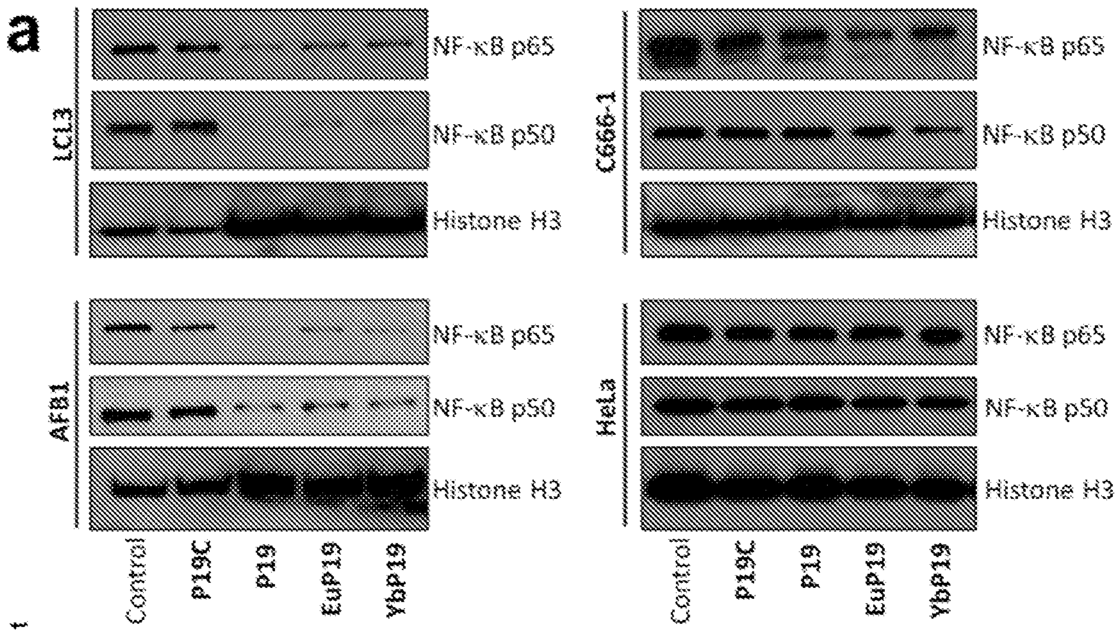
Figure 6:
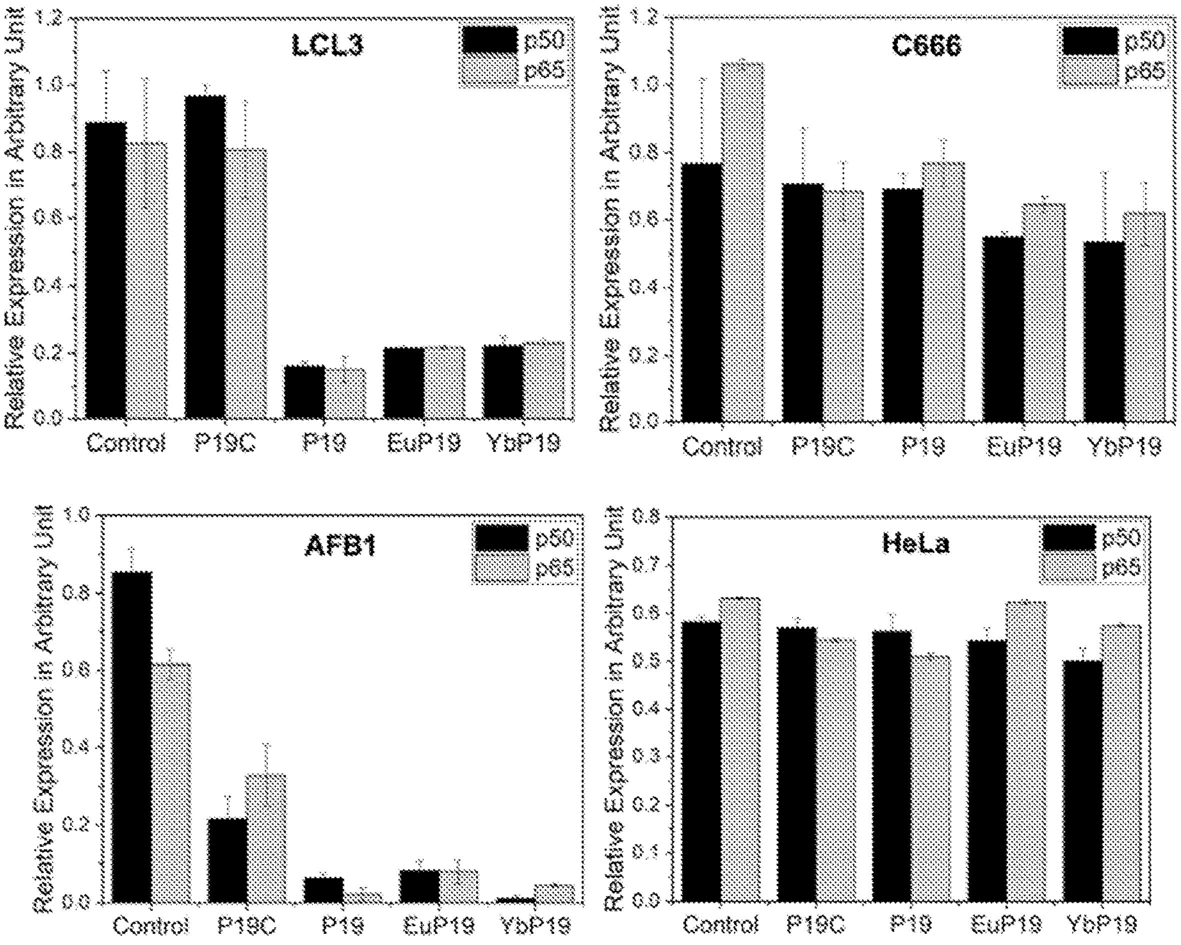

FIG. 6 depicts A) Western blot results and B) the bar chart of NF-κB p65 and p50 in LCL3, AFB1, C666-1 and HeLa after the incubation with 20 μM P19, EuP19 and YbP19 for 30 minutes (preincubation with TNFα, 10 ng/ml for 30 minutes, histone H3 serves as the loading control).

Figure 7:
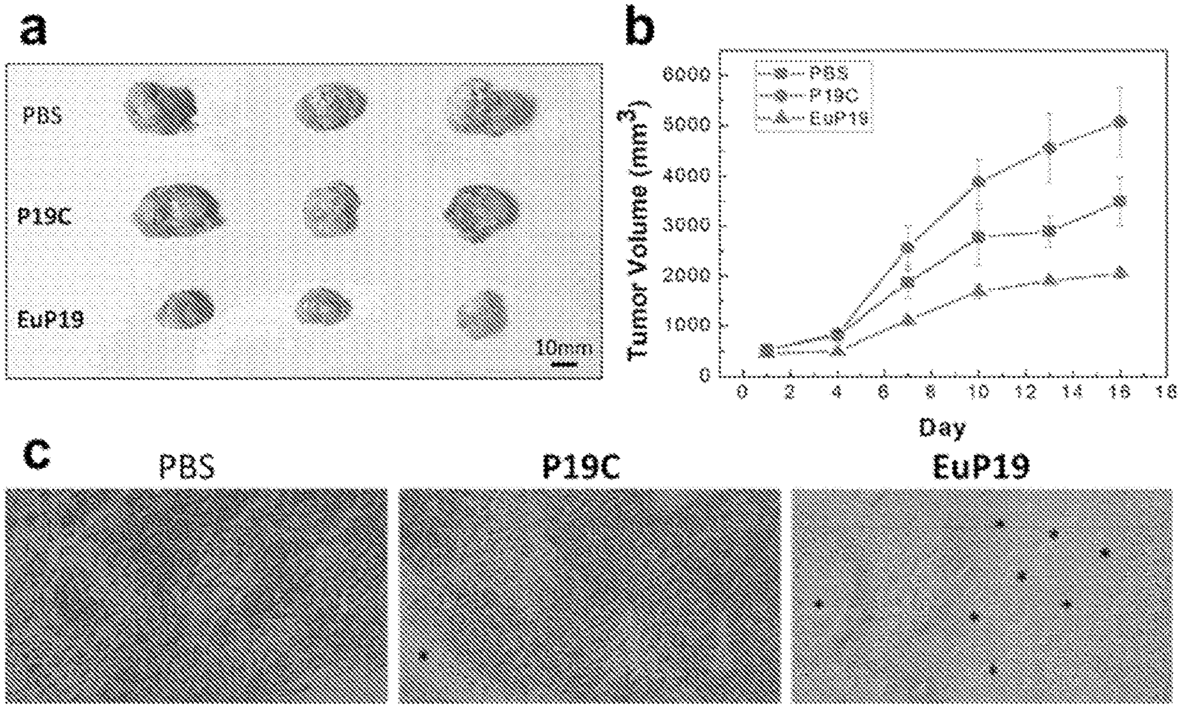

FIG. 7 depicts A) Images of the LCL3-xenograft model in different treatment groups. B) The change in average LCL3 tumor volume of the xenograft model under different treatments, data are expressed as mean±SEM. * refers to P<0.1 vs PBS control, statistically significant difference. C) Representative images of centre region of PBS control, P19C and EuP19 (acellular regions indicated by *) treated tumors formed by LCL3 cells. H&E, hematoxylin and eosin.

Figure 8:
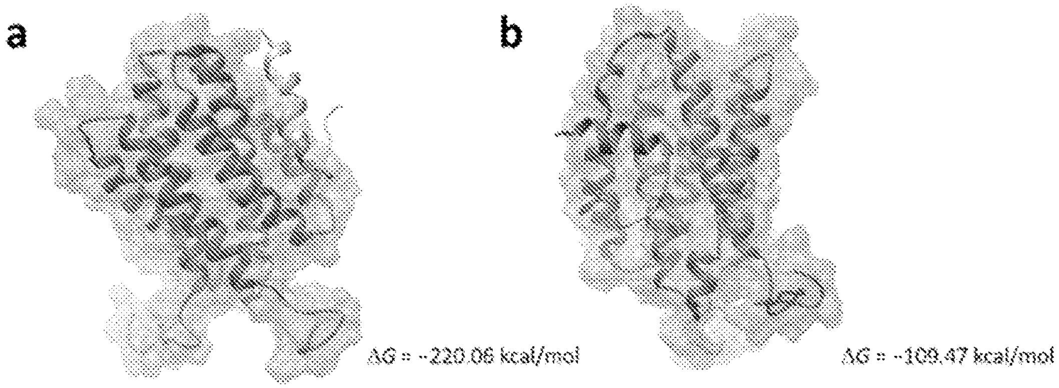

FIG. 8 depicts the docked structure of A) P19 and B) P19C with the LMP1 model with estimated binding energy shown.

Figure 9:
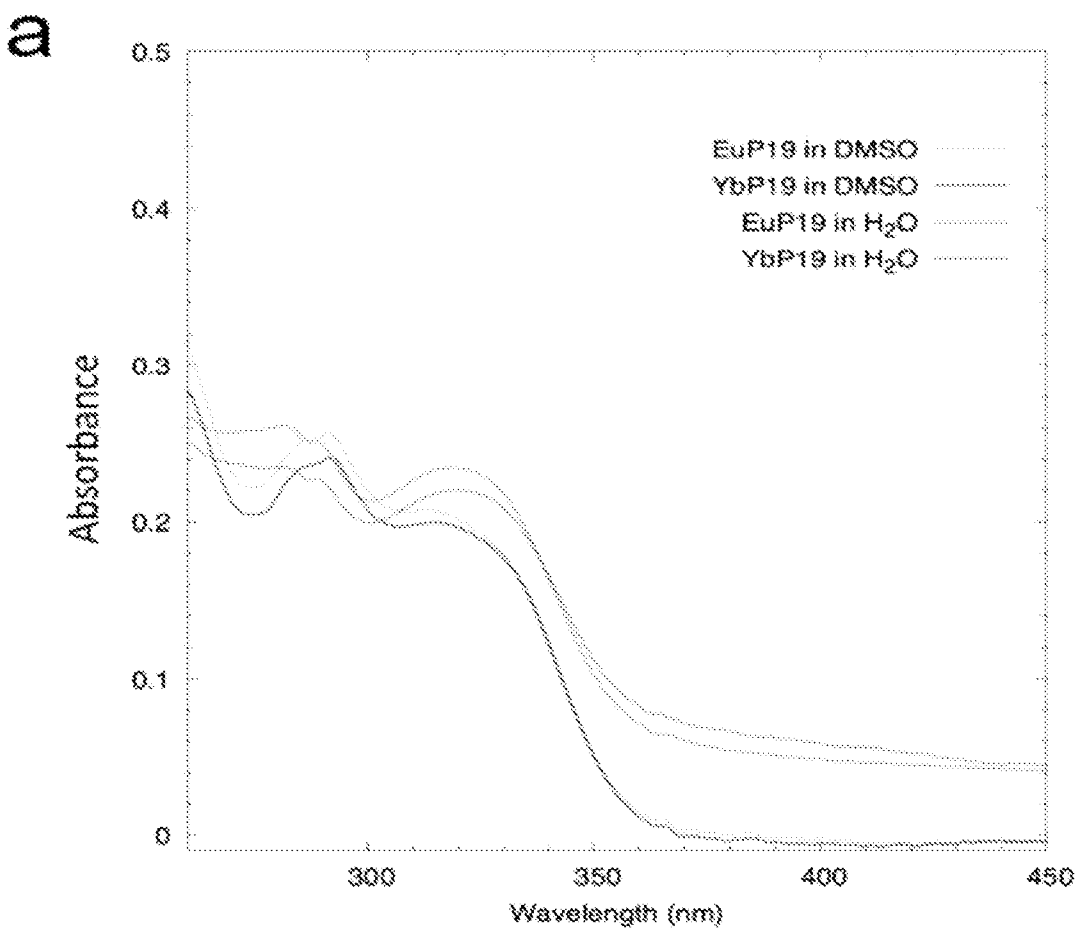
Figure 9:
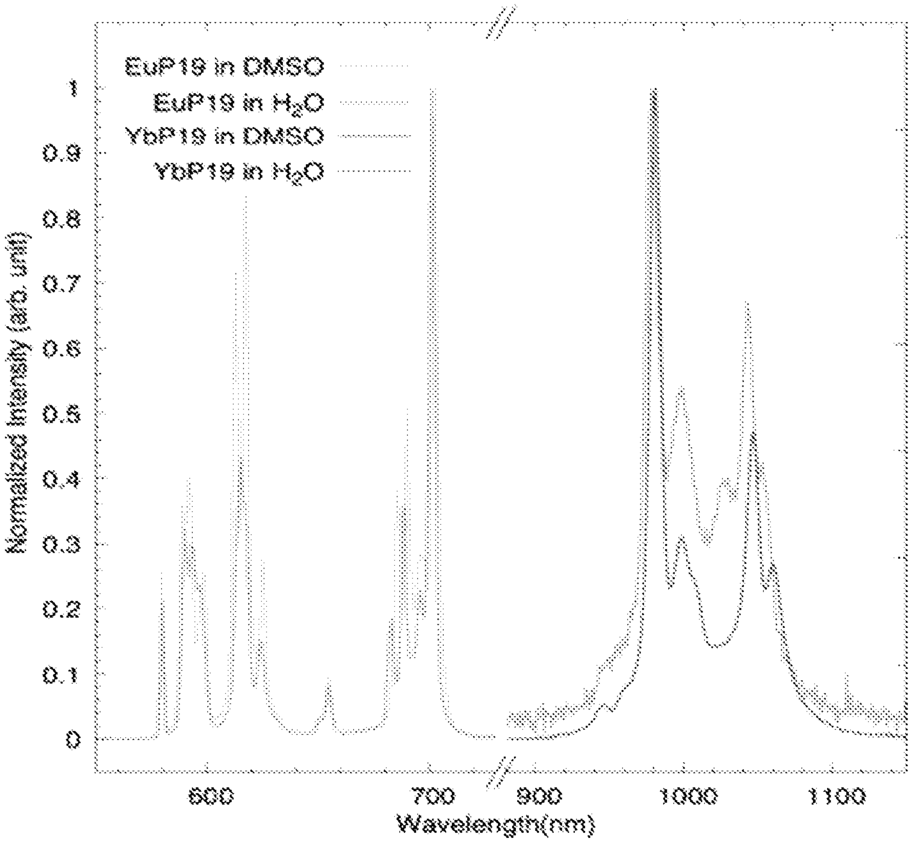

FIG. 9 depicts A) Absorption, B) emission ($\lambda_{ex}$=370 nm) and C) excitation spectra of 10 μM EuP19 and YbP19 in $H_2O$ and DMSO.

Figures 9, 10:
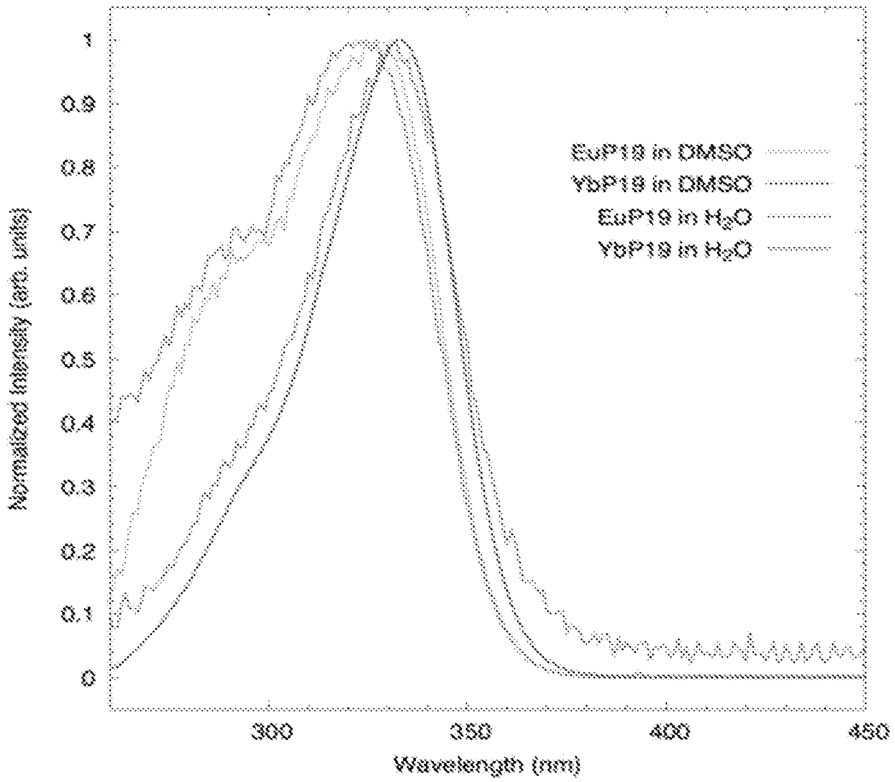

FIG. 10 depicts Table 2 showing the quantum yield of EuP19 and YbP19; Lifetime of EuP19 in $H_2O$ and $D_2O$ and q-value of EuP19.

Figure 11:
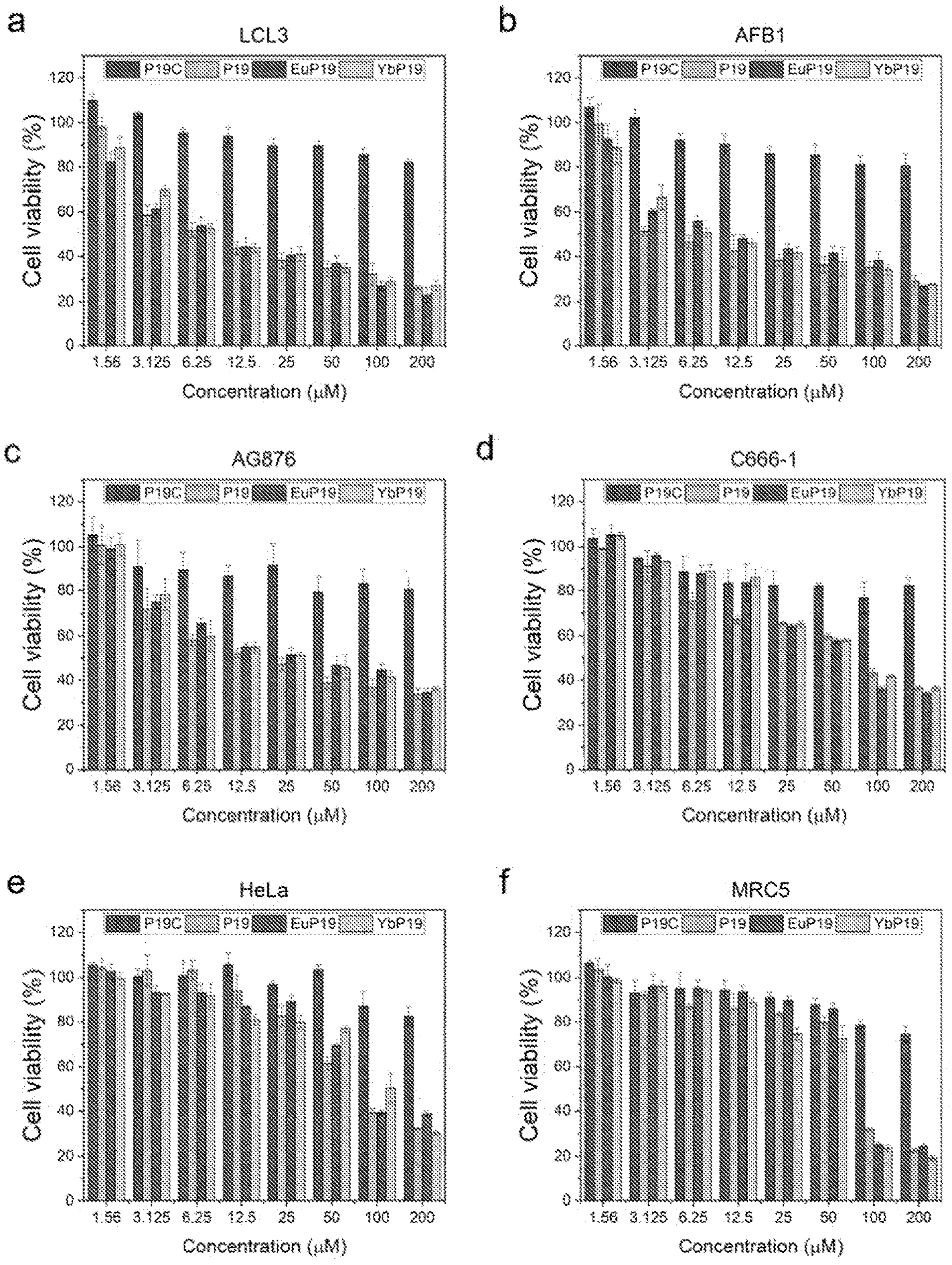

FIG. 11 depicts the cytotoxicity assays of P19C, P19 and EuP19 in LMP1-positive A) LCL3, B) AFB1, C) AG876, D) C666-1 cell lines, and LMP1-negative E) HeLa, and F) MRCS cell lines.

Figure 12:
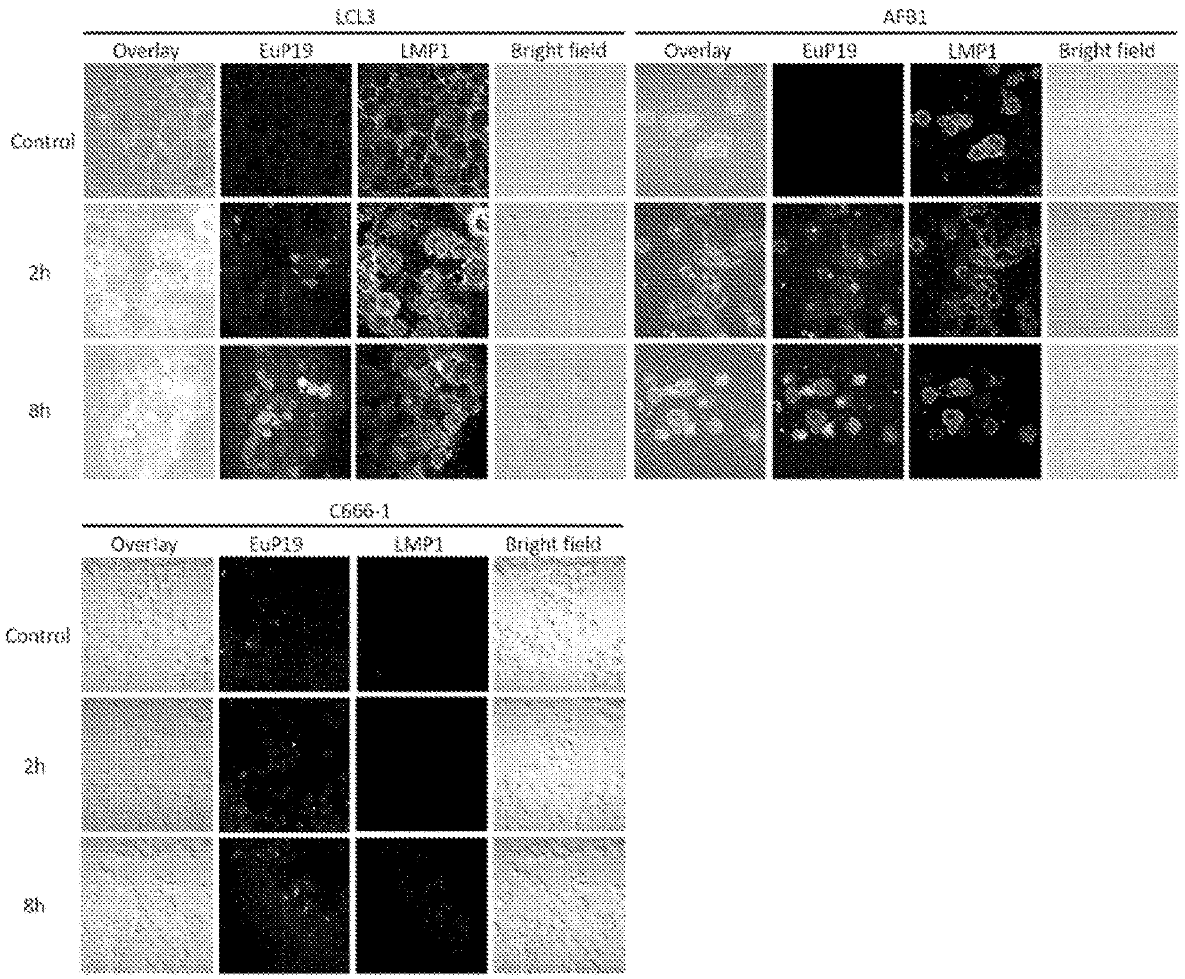

FIG. 12 depicts immunoluminescence imaging of LMP1 protein and EuP19 in LCL3, AFB1 and C666-1 cells at different incubation duration. ([EuP19]=10 μM; $\lambda_{ex}$: 370 nm; $\lambda_{ex}$ of LMP1 staining dye: 491 nm)

Figure 13:
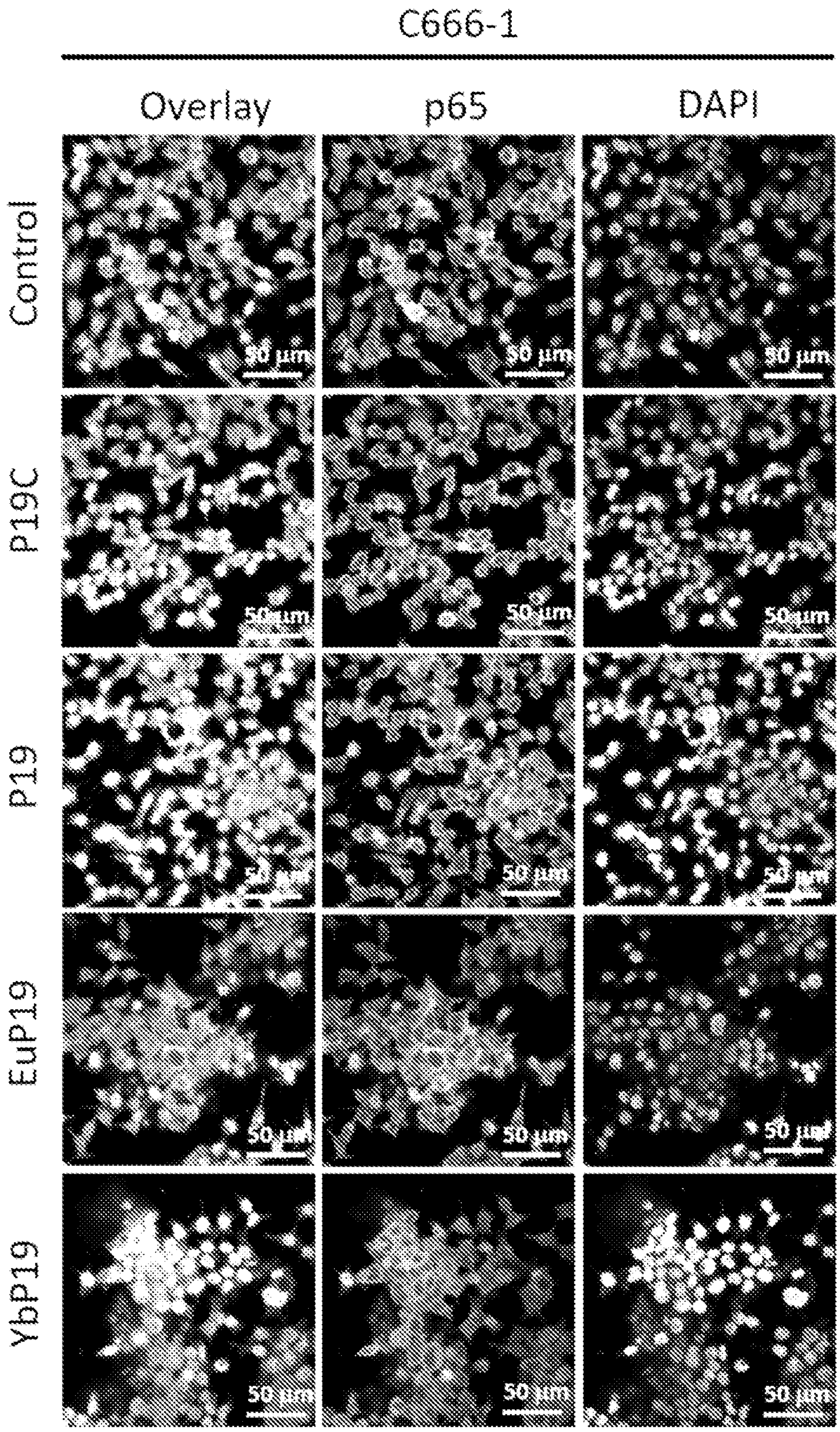

FIG. 13 depicts immunofluorescence imaging of NF-κB p65 in C666-1 cell lines ([P19]=10 M, [EuP19]=10 mM, [YbP19]=10 mM, incubation time=24 h; preincubation [TNFα]=10 ng/ml, incubation time=30 min; $1_{ex}$ of NF-κB staining dye=491 nm; $1_{ex}$ of DAPI=405 nm).

Figure 14:
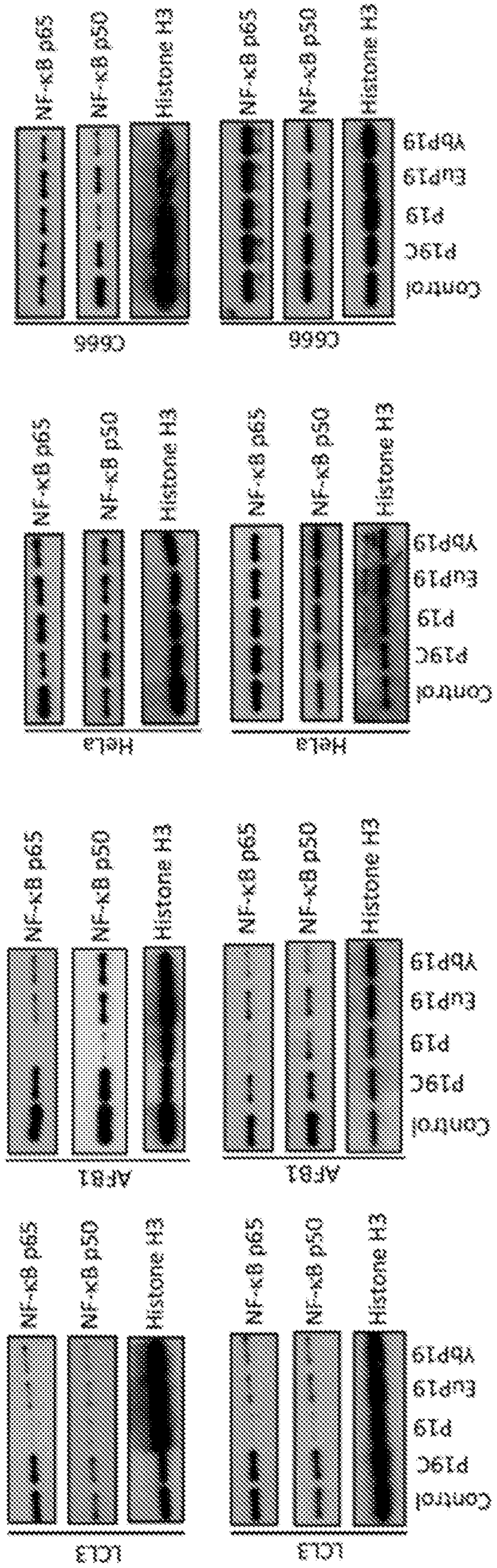

FIG. 14 depicts Western blot results of NF-κB p65 and p50 in LCL3, AFB1, C666-1 and HeLa after the incubation with 20 μM P19, EuP19 and YbP19 for 30 minutes of individual replicates (preincubation with TNFα, 10 ng/ml for 30 minutes, histone H3 serves as the loading control).

Figure 15:
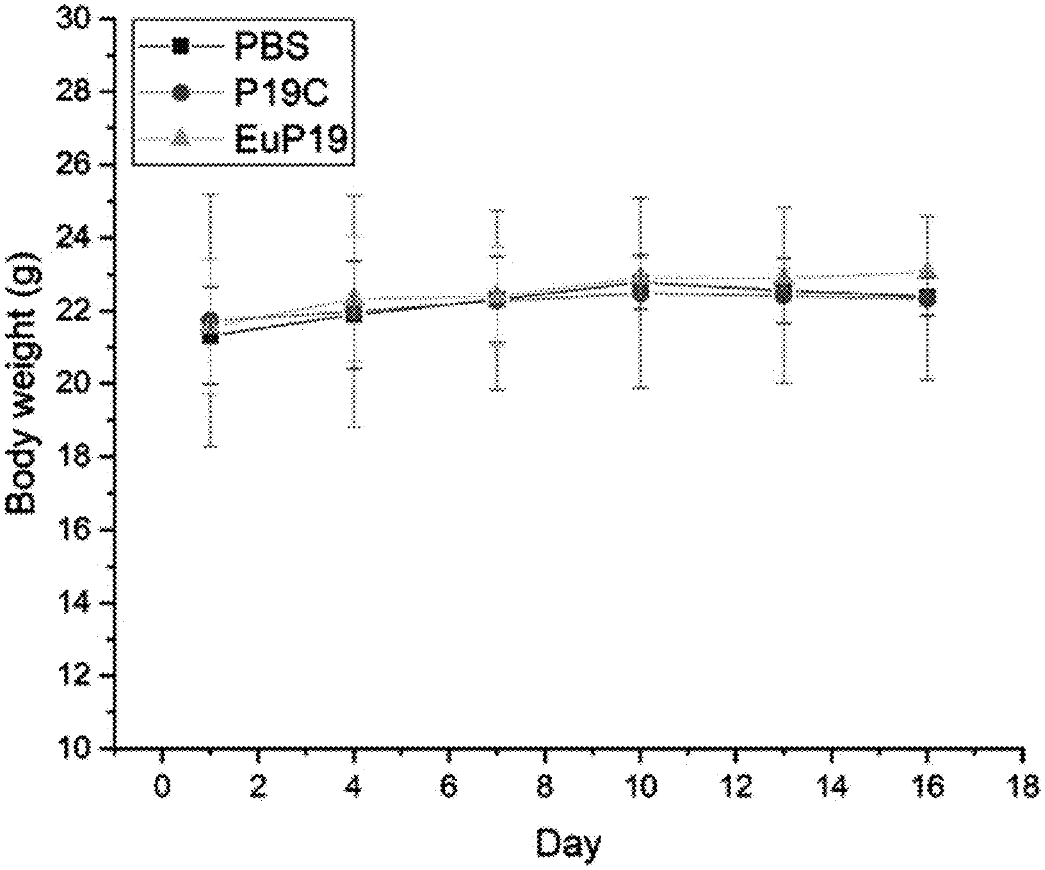

FIG. 15 depicts change in body weight during the in vivo tumour inhibition treatment.

Figure 16:
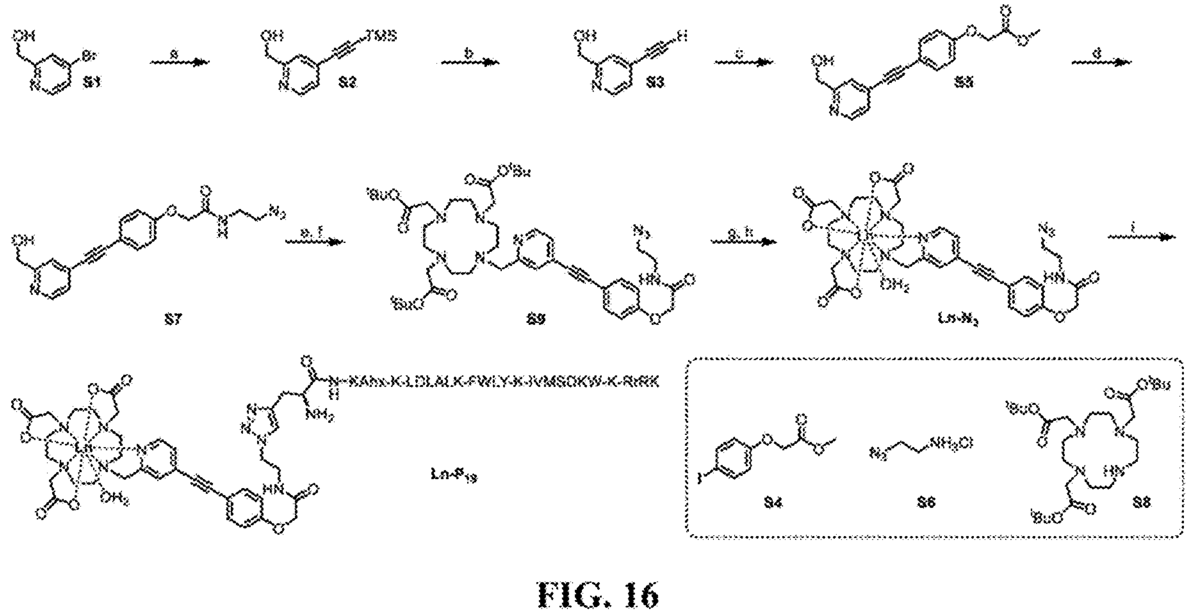

FIG. 16 depicts the synthetic route of desired compounds. Reagent and conditions: a) Ethynyltrimethylsilane, $Pd(PPh_3)_4$, CuI, DIPEA, $N_2$, THF, 45° C., 12 h; b) $K_2CO_3$, MeOH, room temperature, 30 min; c) S4, $Pd(PPh_3)_4$, CuI, DIPEA, $N_2$, 45° C., 12 h; d) S6, TEA, THF/MeCN, v/v, 1/1, 60° C., 2 d; e) MsCl, DIPEA, DCM, room temperature, 30 min; f) S8, $K_2CO_3$, MeCN, 60° C., overnight; g) TFA/DCM, v/v, 1/1; room temperature, overnight; h) $LnCl_3 \cdot 6H_2O$, $MeOH/H_2O$, pH 7~8, v/v, 1/2, room temperature, 24 h; P19 (Pra-KAhx-K-LDLALK-FWLY-K-IVMSDKW-K-RrRK, SEQ ID NO:2), $Cu(CN)_4PF_6$, TBTA, DIPEA, $N_2$, room temperature, 2-4 d.

DETAILED DESCRIPTION

Definitions

The following terms shall be used to describe the present invention. In the absence of a specific definition set forth herein, the terms used to describe the present invention shall be given their common meaning as understood by those of ordinary skill in the art.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., C1-40 alkyl group), for example, 1-30 carbon atoms (i.e., C1-30 alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In certain embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In certain embodiments, aryl groups can be optionally substituted. In certain embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be optionally substituted.

The term "optionally substituted" refers to a chemical group, such as alkyl, cycloalkyl aryl, and the like, wherein one or more hydrogen may be replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and N+($C_{1-4}$alkyl)$_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

The present disclosure provides a polypeptide comprising SEQ ID NO:1, wherein the N-terminus of the residue at position one of SEQ ID NO:1 is covalently bonded to a moiety represented by the structure: X—Y—Z, wherein X is a click residue or a click cycloadduct, Y is a lysine residue; and Z is a linker, and each of the residues at positions one, twelve, and twenty of SEQ ID NO:1 is independently a water-soluble residue selected from the group consisting of lysine, arginine, histidine, aspartic acid, and glutamic acid, wherein the click residue is a moiety of Formula 1:

1

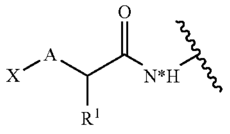

wherein N* is the n-terminal nitrogen of the lysine residue;

A is $(CR^2_2)_m$, aryl, or —$CH_2$-aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl;

X is —$N_3$, —C≡CH, —$OCH_2C$≡CH, —$NHCH_2C$≡CH, —NH(C═O)$OCH_2C$≡CH, —NH(C═O)$NHCH_2C$≡CH, —O(C═O)$OCH_2C$≡CH, or —O(C═O)$NHCH_2C$≡CH; or X is a moiety selected from the group consisting of:

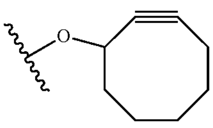

and

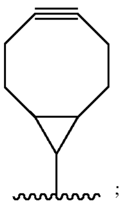

;

and m is a whole number selected from 0-10;

the click cycloadduct is a moiety of Formula 3:

-continued

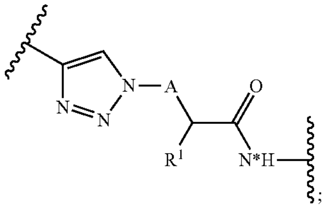

wherein N* is the n-terminal nitrogen of the lysine residue; A is $(CR^2_2)_m$, aryl, or —$CH_2$-aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl; and m is a whole number selected from 0-10; and the linker is a moiety of Formula 2:

2

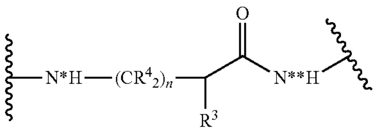

wherein N* is covalently bonded to the c-terminal carbon of lysine residue and N** is covalently bonded to the residue at position one of SEQ ID NO:1;

$R^3$ is hydrogen or amino;

3

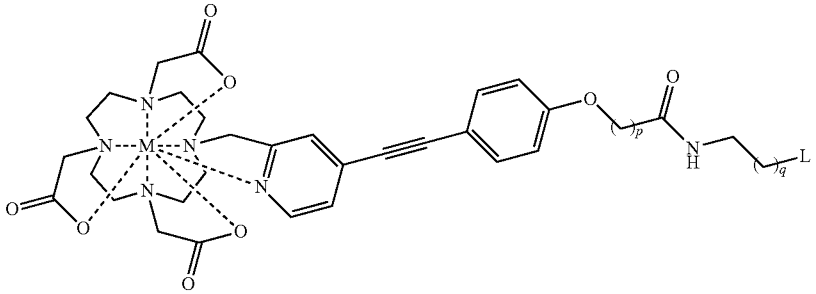

wherein M is a lanthanide or is absent;

p is a whole number selected from 0-6;

q is a whole number selected from 0-6; and

L is a moiety selected from the group consisting of:

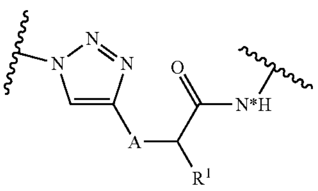

and $R^4$ for each instance is independently hydrogen, alkyl, cycloalkyl, or aryl; or two instances of $R^4$ and the carbons to which they are bonded form a 3-6 membered cycloalkyl; and n is a whole selected from 0-10.

The click residue can be any divalent moiety comprising an alkyne or an azide. In certain embodiments, the click residue is an unnatural amino acid comprising an alkyne or an azide. In certain embodiments, the click residue is a moiety of Formula 1:

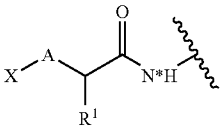

wherein N* is the n-terminal nitrogen of the lysine residue;

A is $(CR^2{}_2)_m$, aryl, or —$CH_2$-aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl;

X is —$N_3$, —C≡CH, —$OCH_2C$≡CH, —$NHCH_2C$≡CH, —NH(C═O)$OCH_2C$≡CH, —NH(C═O)$NHCH_2C$≡CH, —O(C═O)$OCH_2C$≡CH, or —O(C═O)$NHCH_2C$≡CH; or X is a moiety selected from the group consisting of:

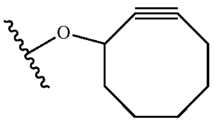 and 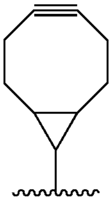 ;

and m is a whole number selected from 0-10.

m can be a whole number selected from 0-10, 1-10, 0-8, 1-8, 0-6, 1-6, 1-5, 1-4, 1-3, 2-6, 4-6, 2-5, 3-5 or 2-4. In certain embodiments, m is 1, 2, 3, or 4.

In instances in which A is aryl or —$CH_2$-aryl, A can be optionally substituted phenyl, optionally substituted napthyl, optionally substituted —$CH_2$Ph, optionally substituted —$CH_2$napthyl.

In certain embodiments, A is a moiety selected from the group consisting of:

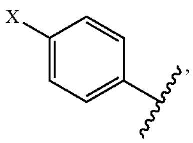, 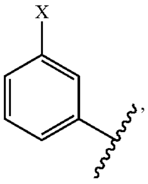, 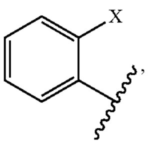, 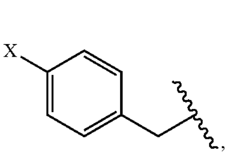, 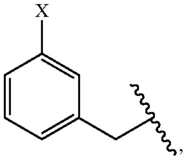, and 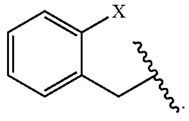.

$R^1$ can be —$NR_2$, wherein R for each instance is independently hydrogen, $C_1$-$C_6$ alkyl, $C_1$-$C_5$ alkyl, $C_1$-$C_4$ alkyl, $C_1$-$C_3$ alkyl, or $C_1$-$C_2$ alkyl. In certain embodiments, $R^1$ is —NHMe, —$NH_2$, or —$NMe_2$.

$R^2$ for each instance can independently be hydrogen, $C_1$-$C_6$ alkyl, $C_1$-$C_5$ alkyl, $C_1$-$C_4$ alkyl, $C_1$-$C_3$ alkyl, $C_1$-$C_2$ alkyl, $C_3$-$C_6$ cycloalkyl, $C_4$-$C_6$ cycloalkyl, $C_5$-$C_6$ cycloalkyl, or $C_6$-$C_{10}$ aryl. In certain embodiments, each $R^2$ is hydrogen.

In certain embodiments, the click residue is selected from the group consisting of:

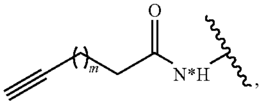, 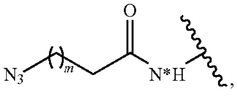, 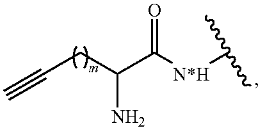, 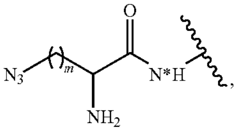, 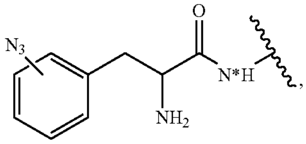, 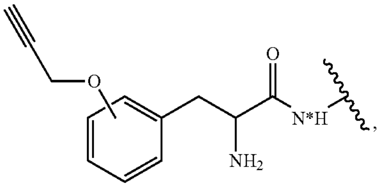, 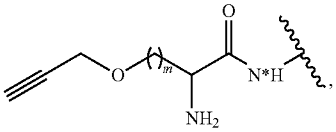, and 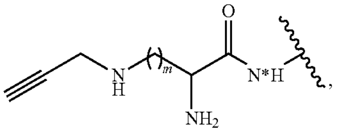, wherein m is a whole number selected from 0-10, 1-10, 0-8, 1-8, 0-6, 1-6, 1-5, 1-4, 1-3, 2-6, 4-6, 2-5, 3-5 and 2-4.

Exemplary click residue moieties include, but are not limited to:

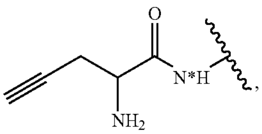, 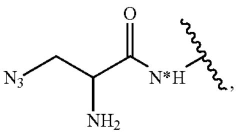, 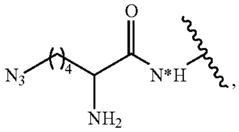, 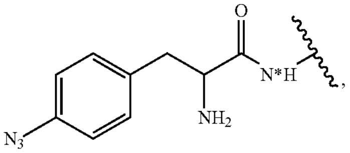,

-continued

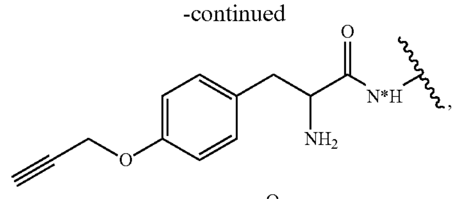

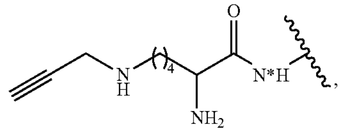

and

-continued

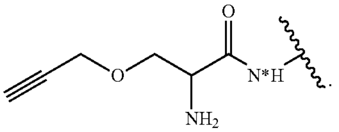

The click cycloadduct can be represented by a moiety of Formula 3:

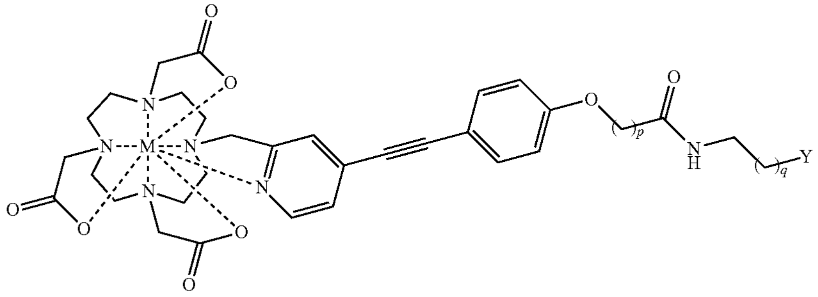

3 wherein M is a lanthanide or is absent;

p is a whole number selected from 0-6;

q is a whole number selected from 0-6; and

L is a moiety selected from the group consisting of:

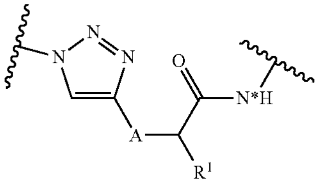

and

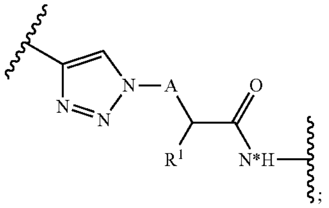

wherein N* is the n-terminal nitrogen of the lysine residue;

A is $(CR^2_2)_m$ or aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl; and m is a whole number selected from 0-10.

In instances in which M is absent, the click cycloadduct can be represented by a moiety of Formula 4:

4

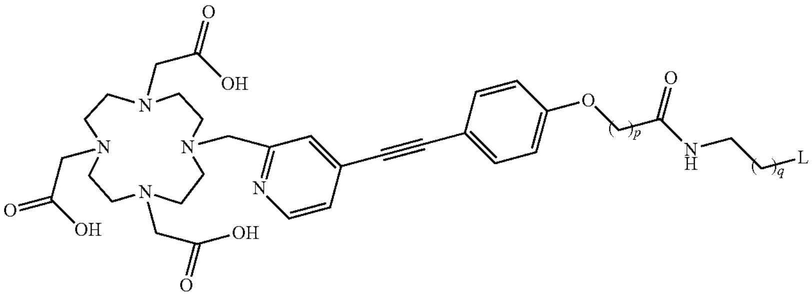

or a pharmaceutically acceptable salt thereof, wherein p, q, and L are each independently defined as described in any embodiment disclosed herein.

In certain embodiments, M a paramagnetic metal ion selected from the group consisting of the lanthanide series, e.g., having an atomic number of 57-70.

M can be in a +1, +2, +3, +4, +5, or +6 oxidation state.

In certain embodiments, M is selected from the group consisting of praseodymium (III), neodymium (III), samarium (III), ytterbium (III), gadolinium (III), terbium (III), dysprosium (III), holmium (III), erbium (III), lanthanum (III), and europium (III). In certain embodiments, M is europium (III) or ytterbium (III).

In instances in which the click cycloadduct has a net charge, one or more pharmaceutically acceptable anions may be present. Examples of pharmaceutically acceptable anions include, but are not limited to, Exemplary pharmaceutically acceptable anions, include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, bromide, chloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

The click cycloadduct must be charged balanced. The ratio of the metal complex to an anion can be represented by the formula $(A^{t+})_U(B^{u-})_T$ wherein t represents the charge of the metal complex, U represents the charge of the anion, U is equal to the absolute value of the charge of the anion and T is equal to the absolute value of the charge of the metal complex. For example, when the metal has a charge of 3+ and the anion is Cl—, which has a charge of −1, the charged balance formula would be $(A^{3+})_t(Cl^-)_3$.

p can be a whole number selected from 0-6, 0-5, 0-4, 0-3, 0-2, or 1-3. In certain embodiments, p is 1.

q can be a whole number selected from 0-6, 0-5, 0-4, 0-3, 0-2, or 1-3. In certain embodiments, q is 1.

L is a moiety resulting from [3+2] cycloaddition of alkyne and azide containing precursors. Since the position of the alkyne and the azide in the [3+2] cycloadduct starting materials can be interposed, two moieties having the general formulas below can result:

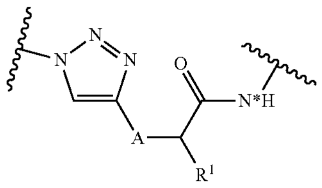

and

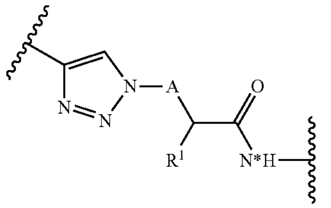

wherein N*, A, and $R^1$ are independently as defined in any embodiment disclosed herein.

In certain embodiments, L is a moiety selected from the group consisting of:

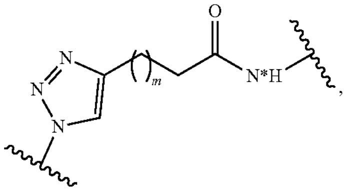

,

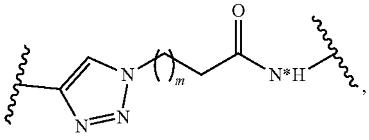

,

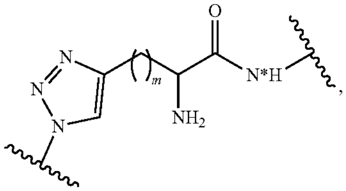

,

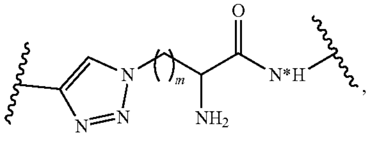

,

-continued

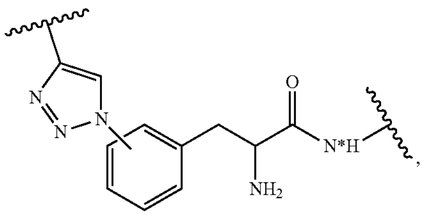

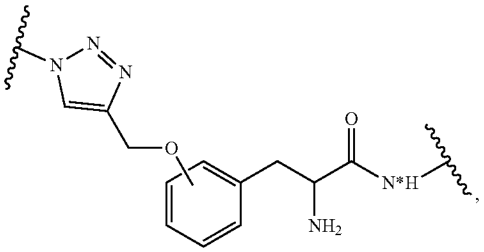

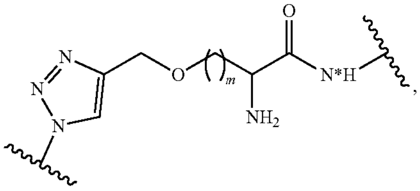

and

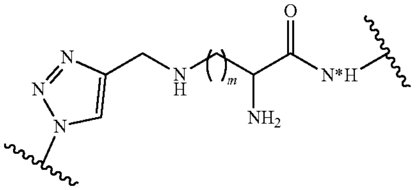

wherein m is a whole number selected from 1-10, 1-9, 1-8, 1-7, 1-6, 2-6, 1-5, 1-4, 2-4, and 1-3. In certain embodiments, m is 1 or 4.

In certain embodiments, L is a moiety selected from the group consisting of:

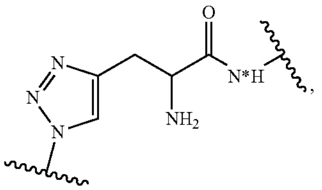

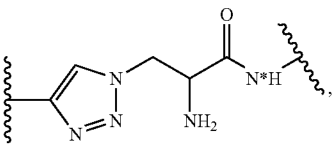

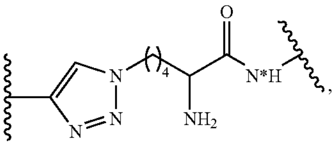

-continued

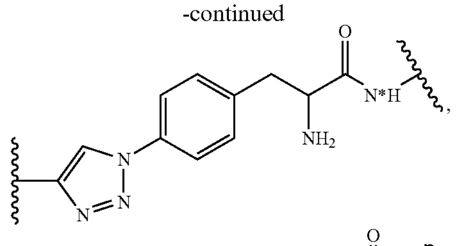

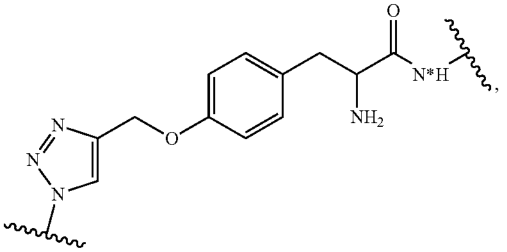

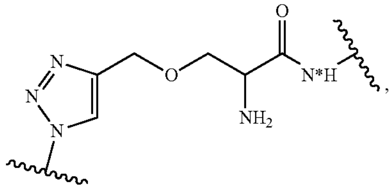

and

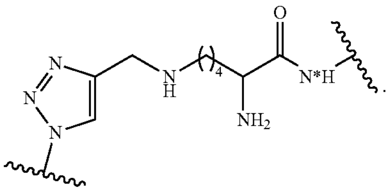

The linker can be any divalent moiety comprising amino and amide functional groups. In certain embodiments, the linker is a moiety of Formula 2:

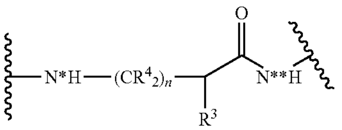

2 wherein N* is covalently bonded to the c-terminal carbon of lysine residue and N** is covalently bonded to the residue at position one of SEQ ID NO:1;

$R^3$ is hydrogen or amino;

$R^4$ for each instance is independently hydrogen, alkyl, cycloalkyl, or aryl; or two instances of $R^4$ and the carbons to which they are bonded form a 3-6 membered cycloalkyl; and n is a whole selected from 0-10.

n can be a whole number selected from 0-10, 1-10, 0-8, 1-8, 0-6, 1-6, 1-5, 1-4, 1-3, 2-6, 4-6, 2-5, 3-5 or 2-4. In certain embodiments, n is 5.

$R^3$ can be hydrogen or —$NR_2$, wherein R for each instance is independently hydrogen, $C_1$-$C_6$ alkyl, $C_1$-$C_5$ alkyl, $C_1$-$C_4$ alkyl, $C_1$-$C_3$ alkyl, or $C_1$-$C_2$ alkyl. In certain embodiments, $R^3$ is hydrogen, —NHMe, —$NH_2$, or —$NMe_2$. In certain embodiments, $R^3$ is hydrogen.

$R^4$ for each instance can independently be hydrogen, $C_1$-$C_6$ alkyl, $C_1$-$C_5$ alkyl, $C_1$-$C_4$alkyl, $C_1$-$C_3$ alkyl, $C_1$-$C_2$ alkyl, $C_3$-$C_6$ cycloalkyl, $C_4$-$C_6$ cycloalkyl, $C_5$-$C_6$ cycloalkyl, or $C_6$-$C_{10}$ aryl. In certain embodiments, each $R^4$ is hydrogen.

In certain embodiments, the linker is a moiety having the structure:

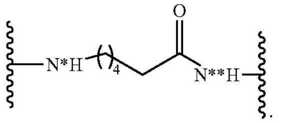

The structure of each of the water-soluble residues is not particularly limited. The water-soluble residues act to improve the overall solubility of the peptide. Each of the water-soluble residues can be a naturally occurring or a non-naturally occurring polar amino acid, a naturally occurring or a non-naturally occurring ionic amino acid (comprises a side chain that exists to some degree in a cationic or an anionic state at physiological pH), or a combination thereof. Exemplary water-soluble residues include, but are not limited to, lysine, arginine, histidine, aspartic acid, and glutamic acid. In certain embodiments, each of the water-soluble residues is independently selected from the group consisting of lysine, arginine, and histidine. In certain embodiments, each of the water-soluble residues is lysine.

The present disclosure also provides a pharmaceutical composition comprising at least one of the polypeptides described herein and at least one pharmaceutically acceptable excipient.

The polypeptides described herein and their pharmaceutically acceptable salts can be administered to a subject either alone or in combination with pharmaceutically acceptable, excipients, carriers, and/or diluents in a pharmaceutical composition according to standard pharmaceutical practice. The polypeptides can be administered parenterally. Parenteral administration includes intravenous, intramuscular, intraperitoneal, and subcutaneous, the preferred method being intravenous administration.

Accordingly, the present disclosure provides pharmaceutically acceptable compositions, which comprise a therapeutically effective amount of one or more of the polypeptides described herein, formulated together with one or more pharmaceutically, excipients, acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, or intravenous as, for example, a sterile solution or suspension, or sustained-release formulation.

As set out herein, certain embodiments of the polypeptides described herein may contain a basic functional group, such as amino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of polypeptides of the present disclosure. These salts can be prepared in situ in the administration vehicle or the dosage form manufacturing process, or by separately reacting a purified polypeptides of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the polypeptides of the present disclosure include the conventional non-toxic salts or quaternary ammonium salts of the polypeptides, e.g., from non-toxic organic or inorganic acids. For example, such conventional non-toxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the polypeptides described herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of polypeptides of the present disclosure. These salts can likewise be prepared in situ in the administration vehicle or the dosage form manufacturing process, or by separately reacting the purified polypeptides in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations include the step of bringing into association a polypeptide described herein with the carrier or excipient and, optionally, one or more accessory ingredients. In general, the formulations are prepared by uniformly and intimately bringing into association a polypeptide of the present disclosure with liquid carriers (liquid formulation), liquid carriers followed by lyophylization (powder formulation for reconstitution with sterile water or the like), or finely divided solid carriers, or both, and then, if necessary, shaping or packaging the product.

Pharmaceutical compositions of the present disclosure suitable for parenteral administration comprise one or more polypeptides described herein in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the polypeptides of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

The present disclosure also provides a method of treating an Epstein-Barr virus infection in a subject in need thereof comprising administering a therapeutically effective amount of a polypeptide described herein to the subject.

Also provided is a method of treating cancer in a subject in need thereof comprising administering a therapeutically effective amount of a polypeptide described herein to the subject, wherein the cancer is an Epstein-Barr virus-associated cancer. The Epstein-Barr virus-associated cancer can be a cancer selected from the group consisting of Burkitt's lymphoma, non-Hodgkin's lymphoma, Hodgkin's disease, T-cell lymphoma, B-cell lymphoma, B-lymphoproliferative disease, NK-cell lymphoma, transplant-associated lymphoproliferative disorders, nasopharyngeal carcinoma, gastric carcinoma, parotid carcinoma, leiomyosarcoma, plasmablastic lymphoma, and primary effusion lymphoma.

The polypeptides described herein are useful for imaging latent membrane protein 1 positive cells. Accordingly, the present disclosure also provides a method of imaging cell suspected of being latent membrane protein 1 positive, the method comprising contacting the cell with a polypeptide described herein; irradiating the cell with electromagnetic radiation having a wavelength within the activation wavelength of the polypeptide; and imaging the fluorescence of the polypeptide. The imaging can occur in vitro or in vivo.

The activation wavelength of the polypeptide can vary depending on its structure, but typically ranges from 300-800 nm.

Upon excitation, the polypeptides described herein can fluoresce in the visible to near infrared range, e.g., 500 to 1,100 nm.

Depending on the wavelength of fluorescence, the step of imaging the fluorescence of the polypeptide can be conducted by visual inspect and/or using a spectrometer. Any conventional spectrometer capable of measure absorbance of the test sample, which can fall between about 500 to 1,100 nm.

Figure 1:
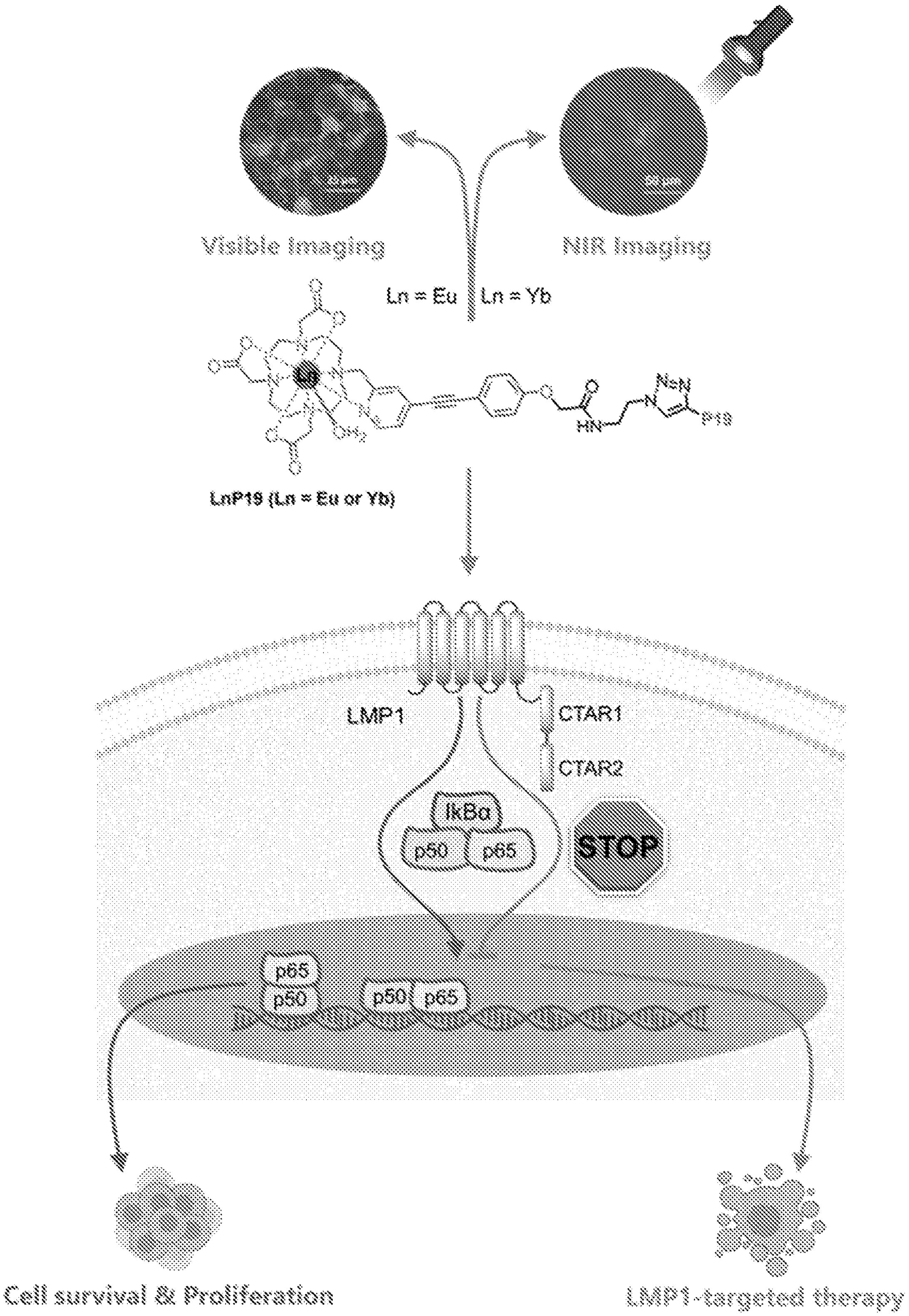
FIG. 1 depicts a schematic diagram of the visible and NIR imaging and the NF-κB inhibition capability of EuP19 and YbP19 on LMP1-positive cells.

Based on the critical role of $FWLY_{38-41}$ (Amino acids 38-41, SEQ ID NO:4) in the signaling pathway regulation, the peptide P19 (Pra-KAhx-K-LDLALK-FWLY-K-IVMSDKW-K-RrRK, SEQ ID NO:2) is designed to mimic the key amino acid residues in the TM1 region of LMP1. Pra is included into the peptide to enable the conjugation of the peptide to the azide group in lanthanide (III) complexes. The incorporation of FWLY (Amino acids 38-41, SEQ ID NO:4) into the peptide can mimic the intermolecular interaction portion of LMP1TM1-2 and LMP1TM3-4, so as to disrupt the oligomerization among the LMP1 monomers in the lipid raft while, inactivate the NF-κB signal transduction (FIG. 1). An extended conformation of FWLY (Amino acids 38-41, SEQ ID NO:4) is adopted to facilitate the α-helix conformation which may have a role in biological functions of LMP1. Besides, lysine and aspartic acid are added to or replaces with some amino acids in the peptide to increase the solubility of the peptide. In the study, a control peptide, P19C (SEQ ID NO:3), is also synthesized by replacing the FWLY (Amino acids 38-41, SEQ ID NO:4) residues with AAAA (Amino acids 10-13, SEQ ID NO:3), which can help to demonstrate the functional significance of the FWLY (Amino acids 38-41, SEQ ID NO:4) motif. With the use of molecular docking, FWLY (Amino acids 38-41, SEQ ID NO:4) in P19 is suggested to interact with TM3-4 region of LMP1 with estimated binding energy of −220 kcal/mol, while, residues AAAA (Amino acids 10-13, SEQ ID NO:3), failing to show an α-helix structure, of P19C (SEQ ID NO:3) interacts with TM1-2 region which considered unable to interrupt the intermolecular oligomerization of LMP1 (FIG. 8). Furthermore, we would also like to determine if P19 can be used for the direct visualization of LMP1.

Immunofluorescence is an assay that relies on the use of antibodies labeled with fluorescent dyes to visualize cellular antigens such as proteins, which can be used for LMP1 imaging. However, the fixation procedure results in cell death, and hence cannot provide real-time information in live cells. In addition, this assay generally cost high and has less flexibility. Luminescence of lanthanide (III) ions offers remarkable advantages for biological optical imaging. Sharp emission bands, large Stokes shift and long luminescence lifetimes (μs to ms range) can benefit the signal-to-noise ratio enhancement of images by abolishing the interference due to the short-lived autofluorescence. A number of anticancer lanthanide (III)-based nano cargoes have been developed for targeting various specific proteins by peptides. However, large size agents including the above-mentioned nanosystems, have the potential risk of interfering with the biological systems. Small-molecule probes offer many benefits, including minimal perturbation to the native function of the target. A methodological approach to construct molecular ytterbium (III)—and neodymium (III)-complexes conjugated with targeting peptide as NIR imaging agents is recently described. The aim of the present study was therefore to develop the lanthanide (III)-based peptide-directed small molecule for the specific Vis/NIR imaging and inhibition via targeting the oncoprotein LMP1. A lanthanide based LMP1-targeting agent with direct imaging function has not been reported. In this work, the inhibitory effects on tumor growth and NF-kB pathway, and the fluorescent properties of our anti-LMP1 compounds on LMP1-positive cell lines are investigated and directly visualized by EuP19 and YbP19.

Figure 2:
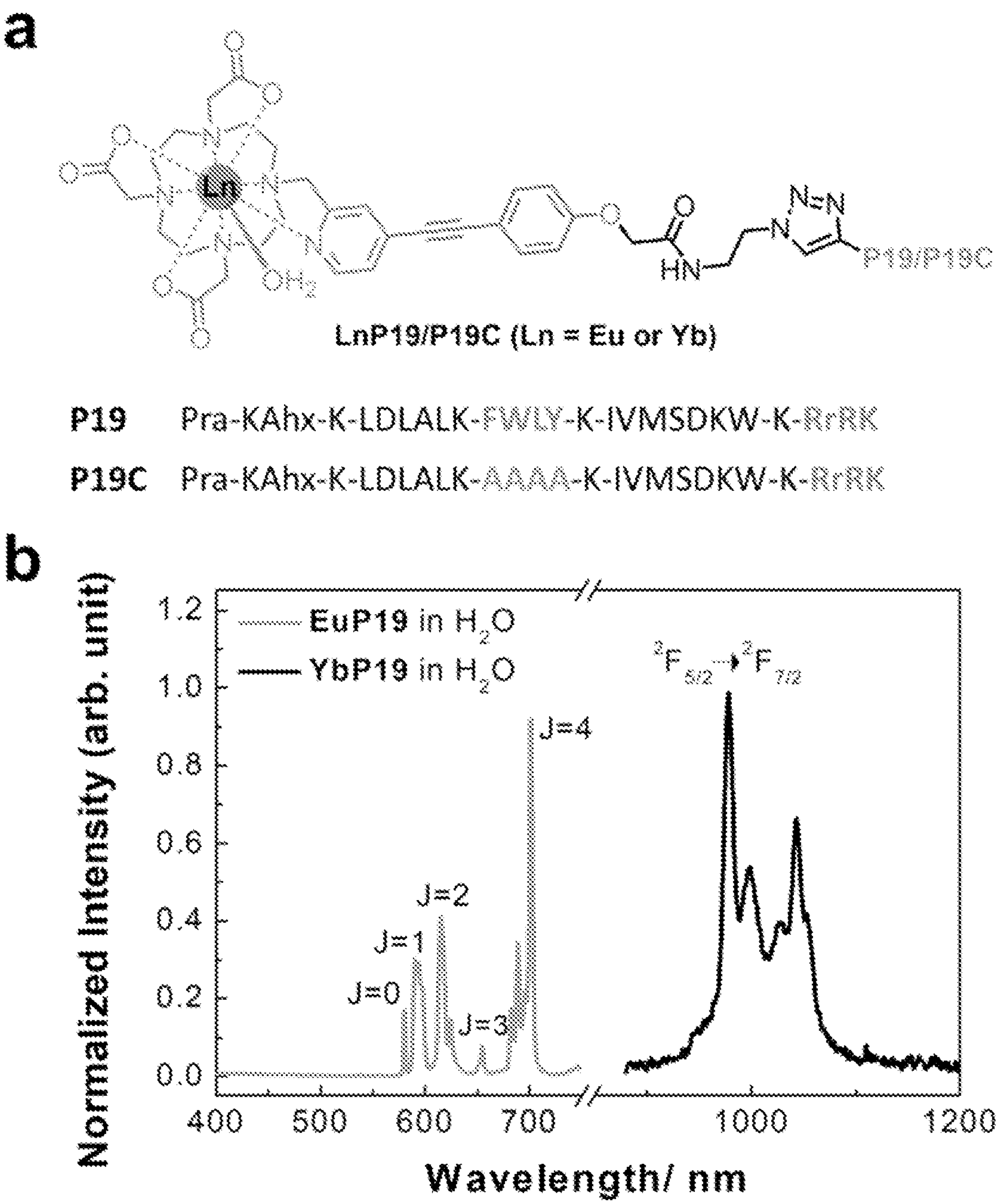
FIG. 2 depicts A) the structure of EuP19, YbP19 and sequence of P19 (SEQ ID NO:2) and P19C (SEQ ID NO:3). B) Emission spectra of EuP19 and YbP19 (10 μM, $\lambda_{ex}$=330 nm).

To synthesize the lanthanide (III)-based luminescent LMP1-targeting probes, the copper (I)-catalyzed alkyne-azide cycloaddition (CuAAC) was conducted to incorporate alkyne-containing P19 [there is an alkyne on the side chain of amino acid residue D-propargylalanine (Pra)] into stable, emissive and azide-containing cyclen-based europium (III) and ytterbium (III) complexes that were used in our previous studies to give the conjugates EuP19 and YbP19 (FIG. 2*a*), respectively, which can simultaneously function as a LMP1 imaging probe as well as a therapeutic agent for EBV-associated cancer treatment. The synthetic route towards LnP19 is shown in FIG. 16. The intermediates are well-characterized by $^{1}H$ NMR and $^{13}C$ NMR spectrometry, the final peptide conjugates are purified via preparative-HPLC, with the well characterization by analytical HPLC and HRMS spectrometry. Emission in visible and near infrared regions of EuP19 and YbP19 are illustrated in FIG. 2*b*, no obvious emission from the ligand and/or protein is observed. The absorption and excitation spectra are included in FIG. 9. The quantum yields of EuP19 and YbP19 are 8.27% and 0.05% respectively. The lifetime of EuP19 in $H_2O$ and $D_2O$ were measured to calculate the q-value equals to 1.05, number of coordinated water molecules (FIG. 10, Table 2).

To study the effects of the designed probes on cell survival, the MTT cytotoxicity assay was carried out in several highly LMP1-positive (LCL3, AFB1, AG876), weakly LMP1-positive (C666-1) and LMP1-negative cell lines (HeLa, MRCS), as shown in FIG. 9. Table 1 summarizes the cytotoxicity of P19C, P19, EuP19, and YbP19 in these cell lines, shown as $LC_{50}$ values. The data reveal that P19, EuP19, and YbP19 possess selective cytotoxicity towards highly LMP1-positive cells as their $LC_{50}$ are 10.3-36.9 μM (FIG. 3, Table 1). On the other hand, their cytotoxicity on weakly LMP1-positive or LMP1-negative cells is relatively low, particularly in C666-1 cells, where the $LC_{50}$ is determined to be >100 μM. P19C with the control peptide not cytotoxic to any of the selected cell lines, because the $LC_{50}$ values are over 200 μM for all selected cell lines. By comparing the cytotoxicity results against P19C, it can be seen that P19, EuP19 and YbP19 are potential in their therapeutic effect on diseases associated with LMP1.

Figure 4:
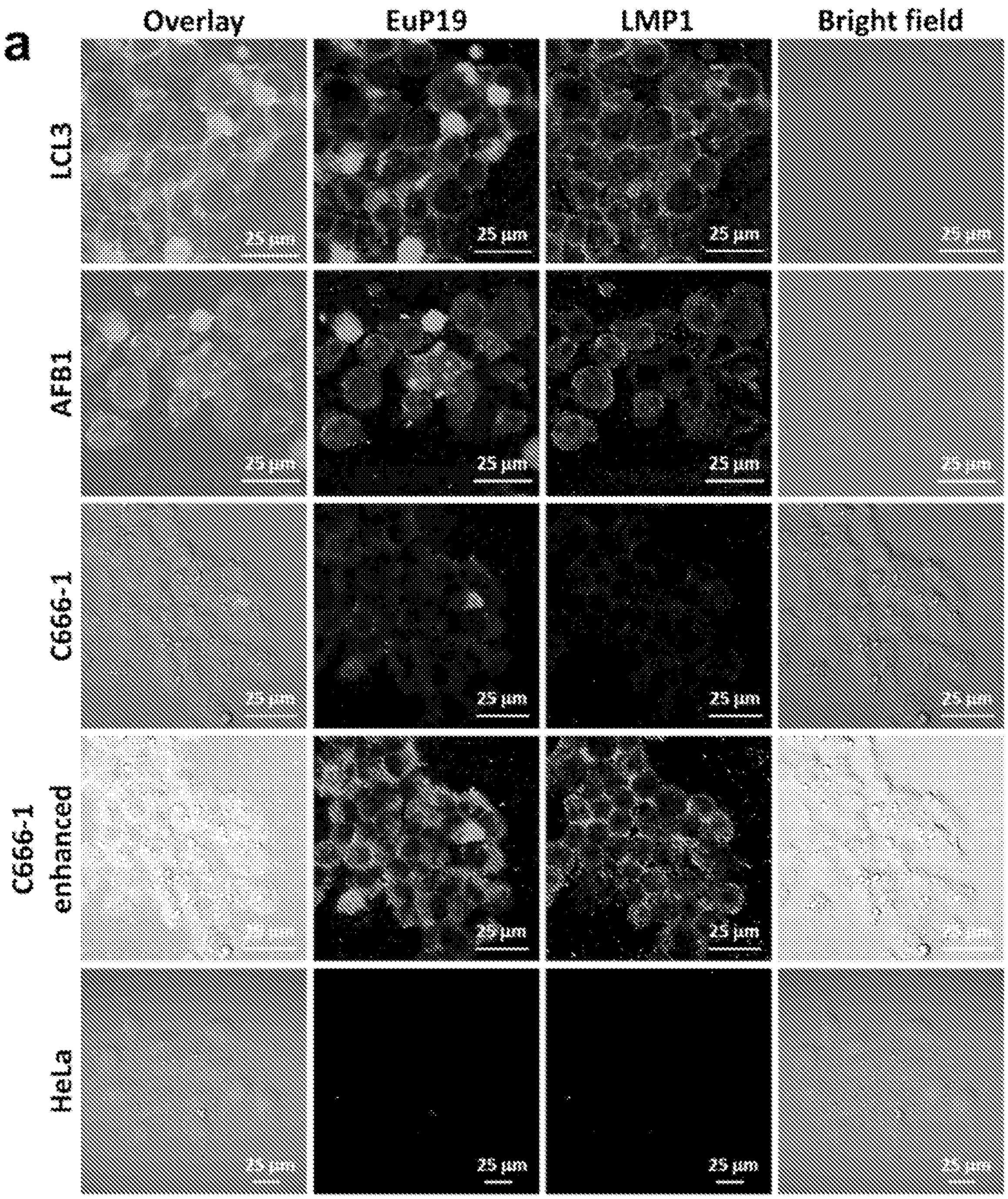
FIG. 4 depicts A) Immunoluminescence imaging of LMP1 protein and EuP19 in LCL3, AFB1, C666-1 and HeLa cells after 12 hours incubation. (Enhanced brightness of luminescence signals in C666-1 is shown underneath the original images for C666-1 cells; [EuP19]=10 μM; $\lambda_{ex}$: 370 nm; $\lambda_{ex}$ of LMP1 staining dye: 491 nm; scale bar: 25 μm). B) Immunoluminescence images of LMP1 and EuP19 in LCL3 in the xy plane with the maximum signal intensity generated from the z stack scanning (scale bar: 25 μm). C) Z stacks of 2D images of LMP1 and EuP19 in LCL3 ([EuP19]=10 μM; $\lambda_{ex}$: 370 nm; incubation time: 12 h; $\lambda_{ex}$ of LMP1 staining dye: 491 nm). D) Imaging of EuP19 in LCL3 by multi-photon microscopy ([EuP19]=10 μM; $\lambda_{ex}$: 740 nm; incubation time: 12 h; scale bar: 50 μm) E) Western blot detection of LMP1 (right) and luminescence signal of EuP19 (left). F) NIR live images of YbP19 in LCL3 cells after different incubation times up 20 hours and NIR images of YbP19 in HeLa after 12 hours incubation ([YbP19]=10 μM; $\lambda_{ex}$: 370 nm; scale bar: 50 μm).
Figure 4:
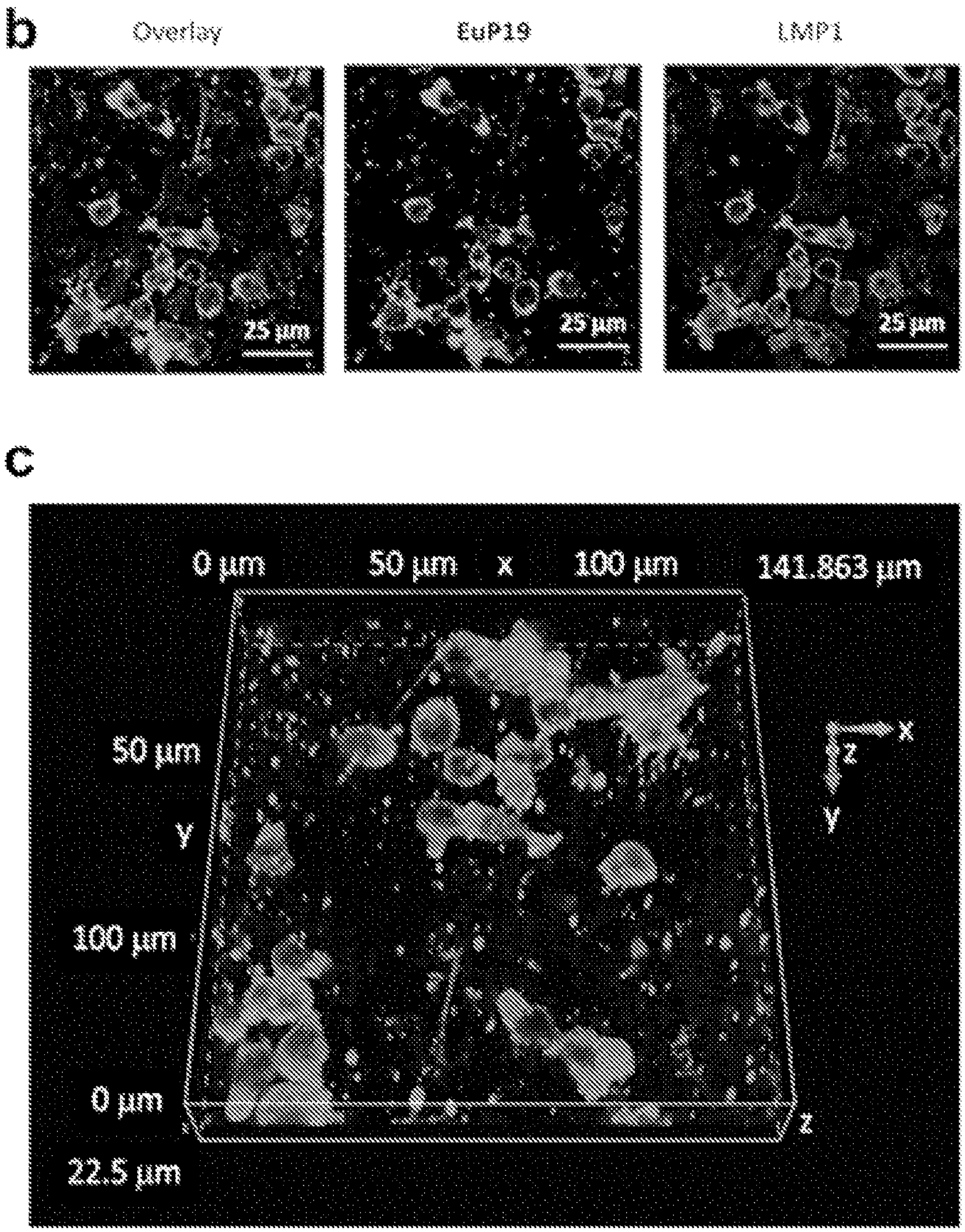
Figure 4:
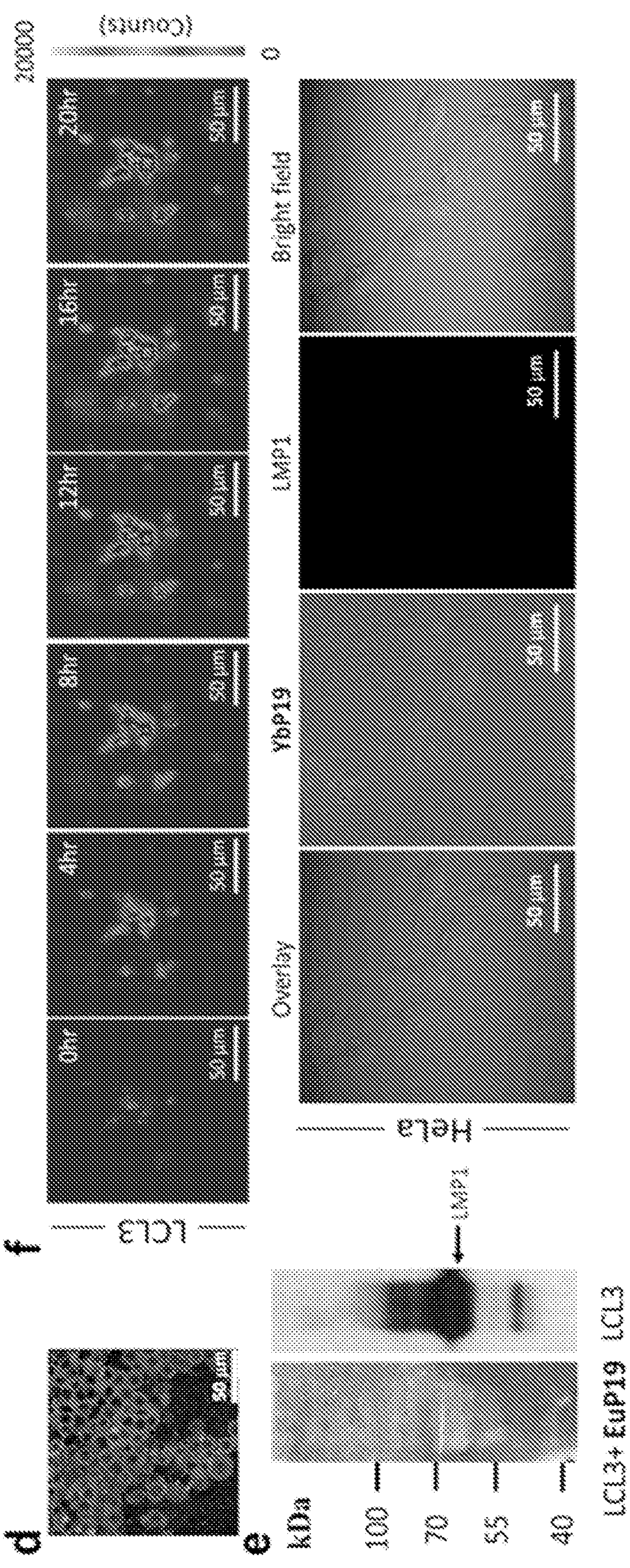

To investigate the subcellular localization of the LMP1-targeting peptide P19, the red-emissive EuP19 was used to determine the application in imaging LMP1. This immunoluminescence imaging experiment of LMP1-overexpressing cells simultaneously allowed us to evaluate the targeting ability of EuP19 for LMP1. First, LMP1-overexpressing cells were incubated with 10 μM of EuP19 for different durations. The sub-cellular localization of LMP1 expression was detected by immunoluminescence imaging. As shown in FIG. 4, overlapping of the LMP1 signal with the EuP19 signal was observed in LCL3 and AFB1 cells upon long incubation time (12 h). (Pearson's coefficients (ranging from −1 to 1): EuP19 in LCL3: 0.341; in AFB1: 0.384). EuP19 is barely detectable in LCL3 cells after 2 hours incubation (FIG. 8). EuP19 was found to co-localize with the LMP1 protein at the LCL3 cell membrane, as reflected by the overlapping signals. The signals from EuP19 in C666-1 cells were much weaker, but the signal was also co-localized with the LMP1 expression as observed in the C666-1 images with enhanced brightness. (Pearson's coefficients (ranging from −1 to 1): EuP19 in C666-1 enhanced: 0.216). However, the absence of signal in both EuP19 and LMP1 was observed in the LMP1-negative HeLa cells (FIG. 4*a*). These imaging results suggest that EuP19 can target the LMP1 protein on cell membranes and may interfere with the downstream signaling transduction pathway(s). In addition, z stacks scanning imaging had been conducted for clear identification of EuP19 co-localization with LMP1 in LCL3 cell. 2D immunoluminescence images of the maximum intensity (FIG. 4*b*) generated from the z stacks of LCL3 after treatment of EuP19 for 12 h (FIG. 4*c*) demonstrate obvious overlapping of the EuP19 and LMP1 signals (Pearson's coefficient: 0.305). In the pursuit of betterment of biological live imaging, the red emissive signal of EuP19 in LCL3 was captured under excitation of the infrared range $\lambda_{ex}$: 740 nm (FIG. 4*d*). The Western blot of LCL3 cells was treated with EuP19 and the luminescence signal was detected (FIG. 4*e* left). Notable binding between EuP19 and LMP1 can be further observed when comparing the Western blot result of LCL3 only conducted with anti-LMP1 detection (FIG. 4*e*, right). Thanks to the near infra-red (NIR) emission from ytterbium (III) in YbP19, NIR live imaging of LMP1 is observed in LCL3 cells with continuous enhancement in NIR signal of LMP1 within 20 hours incubation time (FIG. 4*c*), while nearly no NIR signal can be obtained in the LMP1-negative HeLa cells (FIG. 4*d*). The effective LMP1-targeting and the Vis/NIR imaging ability makes EuP19 and YbP19 the first lanthanide-based bio-probes for direct LMP1 visualization and monitoring of LMP1-associated cancers.

Figure 5:
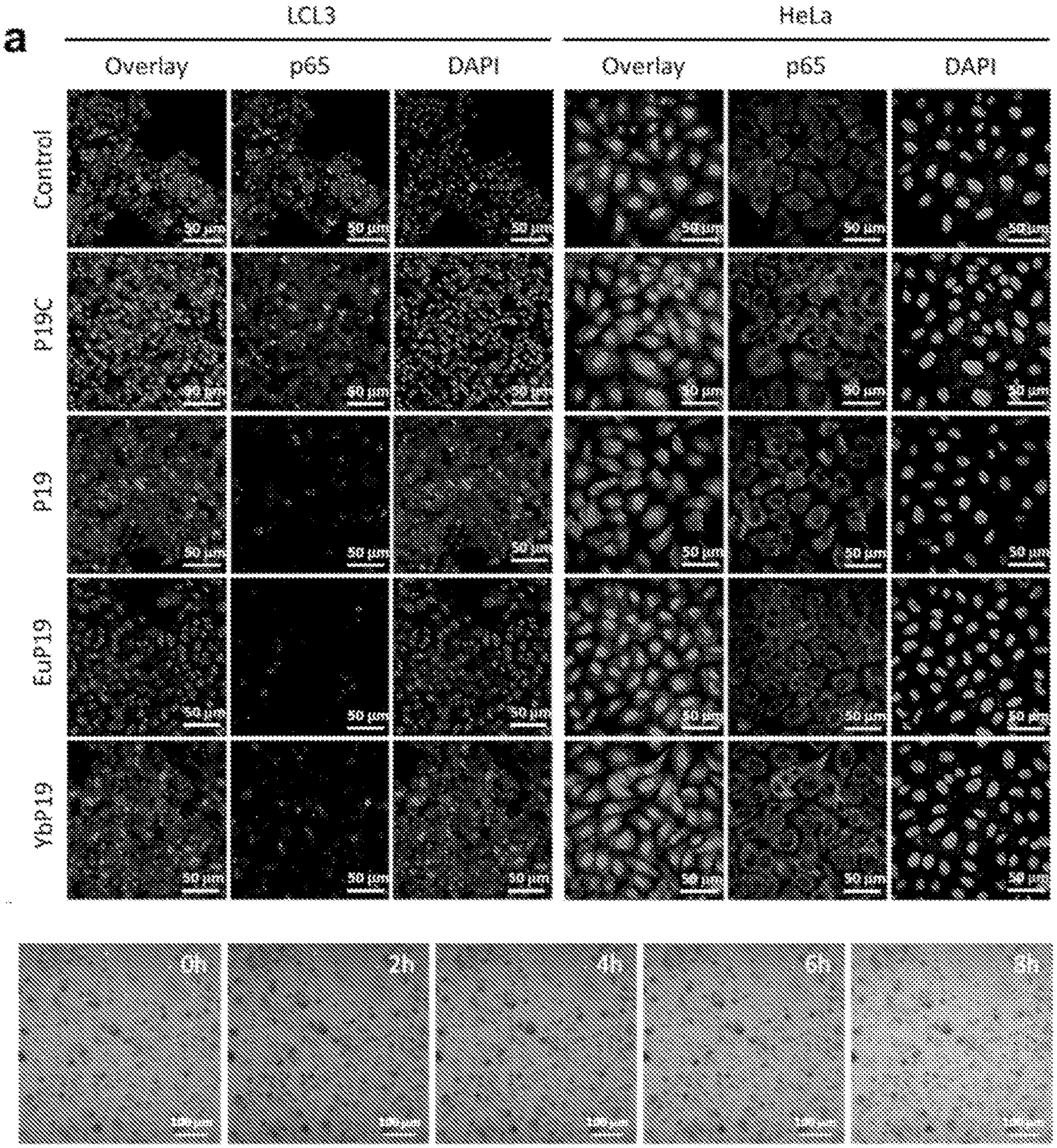
FIG. 5 depicts A) Immunofluorescence imaging of NF-κB p65 in LCL3 and HeLa cell lines ([P19]=10 [EuP19] and [YbP19]=10 incubation time=24 h; preincubation [TNFα]=10 ng/ml, incubation time=30 mins; $\lambda_{ex}$ of NF-κB staining dye=491 nm; $\lambda_{ex}$ of DAPI=405 nm; scale bar: 50 μm). Some fluorescence is from p65 while other fluorescence is from DAPI, a nucleus dye serving as the control. B)

We then investigate the inhibitory effects of our anti-LMP1 conjugates on the NF-κB pathway, which is one of the major pathways that EBV has hijacked for promoting cell growth and proliferation in EBV-associated tumours. Since NF-κB is typically activated by the canonical pathway which involves the nuclear translocation of the heterodimer of p50 and p65, immunofluorescence imaging of NF-κB p65 was then performed. Tumour necrosis factor alpha (TNFα) was added to these tumour cells, so as to activate the NF-κB pathway. As shown in FIG. 5*a*, there was significant suppression of the green fluorescence (appeared as white dot in this specification) p65 signal in LCL3 in the presence of P19, EuP19 and YbP19. However, no significant effect was observed with P19C and in the control group without any compound. Furthermore, when using the pTRE-EGFP reporter to detect NF-κB activity, the results showed that the green fluorescent (appeared as white dot in this specification) protein (GFP) signals were decreased when LCL3 was treated with P19 for 6 hours (FIG. 5*b*), suggesting that P19 can greatly suppress both the expression of NF-κB p65 and its activity. In contrast, strong green fluorescence (appeared as light grey in this specification) was observed in LMP1-negative HeLa cells (FIG. 5*a*) and weak LMP1-expressing C666-1 cells (FIG. 9), showing that P19 did not exhibit any effect on the NF-κB pathway in the cell lines with low levels of LMP1 expression. The results of using EuP19 and YbP19 were similar to those of P19, demonstrating the great potential of these two conjugates as both LMP1-specific NF-κB inhibitors and imaging agents.

Western blot analysis was also carried out to validate the above imaging results for the components in NF-κB pathway. The LMP1-overexpressing LCL3 and AFB1 cell lines were used for this analysis. The cells were pre-treated with TNFα (10 ng/mL; incubated with the cells for 30 min for activation of the NF-κB pathway before the addition of P19C, P19, EuP19, and YbP19). After 24 hours incubation, the nuclear extracts were separated for each treatment, and the expression of NF-κB p65 and p50 was detected by Western blot analysis. Results showed the nuclear p65 and p50 expression in LCL3 and AFB1 were significantly weakened after being treated with P19, EuP19 and YbP19, compared with the control (FIG. 6). Furthermore, there was no obvious change in the expression of these two proteins when P19C was used. Whereas the changes in expression of p65 and p50 were relatively minor in C666-1 and HeLa cells (FIG. 6). Western blots of individual replicates for NF-κB p65 and p50 in different cell lines were illustrated in FIG. 14. Altogether, the Western blot results are coherent with the immunostaining of NF-κB p65 evidenced in the imaging experiments, indicating that P19, EuP19 and YbP19 can suppress the expression and activity of NF-κB p65 and p50 in cell lines with high levels of LMP1. The reduction in NF-κB activity can contribute to the cytotoxicity of the three compounds towards LMP1-overexpressing cells.

The LCL3-derived xenograft mouse model was used to examine the inhibitory effect of EuP19 in vivo. EuP19, P19C and PBS were administered to three groups of LCL3 xenografts by intratumor injection twice per week under the dosage of 25 μg/tumor. Representative tumor pictures were taken after the treatment. Results illustrate an obvious decrease in the tumor sizes of the EuP19 treatment group (FIG. 7*a*). On day 16, the average tumor volume of this group was significantly lower than those of the two control groups (i.e., PBS and P19C) (FIG. 7*b*). This outcome is in agreement with the in vitro cytotoxicity results, showing that EuP19 can effectively inhibit both in vitro and in vivo growth of LMP1-overexpressing tumor cells. In addition, cell necrosis can be observed in tumor nodules in the LCL3 xenografts treated with EuP19 (FIG. 7*c*). It may associate with the cytotoxic activity of EuP19. However, tightly packed cancer cells can be found in the control tumors (FIG. 7*c*). Besides, there is no significant effect on the mice body weight after treatment with EuP19 when compared with the control groups (FIG. 10), indicating this dosage of EuP19 is safe for the animal. Therefore, EuP19 is considered as a safe and specific theranostic agent to treat LMP1-positive tumors.

The FWLY (Amino acids 38-41, SEQ ID NO:4) amino acid residues were included in P19, which functions as a decoy to mimic the TM1-2 region of LMP1. That design can contribute to the binding with LMP1. The self-association of LMP1 monomer will be disrupted when the LMP1 TM3-4 regions in one monomer binds with P19 via the FWLY (Amino acids 38-41, SEQ ID NO:4) residues, instead of binding with the TM1-2 regions of another LMP1 monomer. The downstream signal transduction, including the canonical NF-κB pathway, can then no longer be stimulated since P19 is lacking the functional LMP1 C-terminus. Inhibition of the oncogenic NF-κB pathway can significantly inhibit cell proliferation in LMP1-overexpressing cells, thus leading to high cytotoxicity. We have made use of emissive europium (III) or ytterbium (III) chelates conjugated with the LMP1-specific peptide P19 to test for their imaging capabilities in various LMP1-expressive and non-expressive cells. The imaging results demonstrate for the first time the feasibility of direct and real-time visualization of LMP1 in EBV-infected cells. Our imaging results confirmed that EuP19 was co-localized with expressed LMP1, which was primarily present at the cellular membrane of the three LMP1-positive cell lines (LCL3, AFB1, C666-1).

However, differences were observed between the various cells. For instance, the red emission of EuP19 generated from C666-1 was weak, contrary to what was observed with LCL3 and AFB1, which clearly reflects the weak membrane LMP1 expression of C666-1 and confirms the localization of the luminescent bio-probe on the membrane. Therefore, not only the subcellular localization, but also the signal intensity of EuP19, correlate well with the LMP1 expression. The weak LMP1 expression seems to make C666-1 cells unresponsive to our compounds, as seen in other LMP1-positive cell lines. In C666-1 cells, a frameshift mutation was identified in CYLD, a negative regulator of NF-κB pathway, resulting in complete loss of CYLD protein expression in this cell model. It is likely that this NF-κB pathway aberration has already replaced the role of LMP1 in activating the NF-κB pathway for tumor growth. That could explain why this particular cell line did not respond well to the anti-LMP1 agents, and also why only a portion of NPC tumors are LMP1-positive (~25 to 40%). The absence of LMP1 expression has the advantage for tumor cells to escape from immune cell recognition.

While P19 possesses great potential in therapeutic intervention due to its selective growth inhibition for LMP1-overexpressing cells, EuP19 and YbP19 with similar cell cytotoxicity offer the additional advantage of visualization of LMP1, which will be beneficial for monitoring the treatment efficacy. EuP19 was also found to inhibit tumor growth on the LMP1-overexpressing LCL3 xenograft model, suggesting that the therapeutic properties of P19 is retained after appending onto the europium (III) complex.

By traditional chromogenic immunohistochemical (IHC) methods, the detection of LMP1 in NPC cases varies between 20-60%. The low detection rates of LMP1 in NPC is probably due to the low levels of LMP1 expression in some NPC tissues, which cannot be detected by conventional IHC. Those low levels of LMP1 expression are sufficient to activate the NF-κB-mediated cell growth and survival. Importantly, LMP1 protein is detected in almost all premalignant or preinvasive NPC tissues, suggesting the contribution of LMP1 during the early stage of NPC pathogenesis. Our LMP1-specific therapeutic probes EuP19 and YbP19 were demonstrated a high potential to provide a much more sensitive means of detection of the low LMP1 expression in NPC tissues which cannot be detected by conventional IHC. Moreover, our new LMP1 probes can also be used for early detection of NPC tumors with LMP1 expression. Our study represents the first live visualization of LMP1 in EBV-positive tumor cells. On the other hand, LMP1-positive tumors are known to be more progressive than LMP1-negative tumors and prone to lymph node metastasis. They are associated with poor overall survival, and LMP1 is also a strong risk factor for poor prognosis in NPC. Our LMP1 probes exhibit high cytotoxicity towards LMP1-expressing cells by suppressing the NF-κB pathway, and these probes can contribute to the therapeutic potential against advanced NPC with poor survival under conventional therapies.

EXPERIMENTAL

The synthetic route is outlined in FIG. 16. Briefly, the azide-containing antenna (compound S7) was constructed via a multi-step synthesis including two Sonogashira couplings and direct amination of methyl ester with an azide-containing linker (compound S6). The antenna was then installed onto the cyclen core (tBu-$DO_3A$, S8), and the corresponding lanthanide complexes (Ln-$N_3$) were obtained after deprotection of tert-butyl ester and coordination with lanthanide ion. Finally, the CuAAC reaction was carried between the azide on lanthanide complexes and the alkyne on peptide (from side chain of Pra, propargylglycine) to give the desired lanthanide-peptide conjugates.

Example 1—Synthesis of (4-((trimethylsilyl)ethynyl)pyridin-2-yl)methanol (S2)

Under inert atmosphere, a mixture of (4-bromopyridin-2-yl)methanol (51, 10 mmol), ethynyltrimethylsilane (12 mmol), $Pd(PPh_3)_4$ (0.1 mmol), CuI (0.05 mmol), and DIPEA (20 mmol) in THF (50 mL) was heated at 45° C. overnight. Upon completion, the reaction mixture was filtered, and the filtrate was concentrated and purified by column chromatograph on silica gel (eluent: hexane/EA, v/v, 3/1 to 1/1), to give the desired product. White solid. Yield 71%. $^1H$ NMR (400 MHz, chloroform-d) δ 8.49-8.44 (m, 1H), 7.33-7.29 (m, 1H), 7.20 (dd, J=5.2, 1.5 Hz, 1H), 4.72 (s, 2H), 4.13-4.06 (m, 1H), 0.25 (s, 9H); $^{13}C$ NMR (101 MHz, chloroform-d) δ 159.42, 148.43, 131.94, 124.46, 122.79, 101.91, 100.14, 64.05, −0.34.

Example 2—Synthesis of (4-ethynylpyridin-2-yl)methanol (S3)

To a solution of (4-((trimethylsilyl)ethynyl)pyridin-2-yl)methanol (S2, 10 mmol) in MeOH (50 ml), $K_2CO_3$ (20 mmol) was added in one portion at 0° C. The mixture was then stirred at room temperature for 30 min. The reaction was monitored by TLC (eluent: hexane/EA, v/v, 1/1). Upon completion, the solvent was vaporized, and then extracted with DCM/water. The organic layer was combined and concentrated, then purified by column chromatography on silica gel (eluent: hexane/EA, v/v, 3/1 to 1/1), to give the desired product. White solid. Yield 87%. $^{1}$H NMR (400 MHz, chloroform-d) δ 8.52 (dd, J=5.1, 0.9 Hz, 1H), 7.34 (dd, J=1.6, 0.9 Hz, 1H), 7.26 (dd, J=5.3, 1.4 Hz, 1H), 4.75 (d, J=3.6 Hz, 2H), 3.78 (d, J=4.7 Hz, 1H), 3.29 (s, 1H); $^{13}$C NMR (101 MHz, chloroform-d) δ 159.79, 148.60, 131.12, 124.76, 123.11, 82.06, 82.02, 64.08.

Example 3—Synthesis of methyl 2-(4-iodophenoxy)acetate (S4)

The suspension of 4-iodophenol (20 mmol), methyl 2-bromoacetate (22 mmol) and $K_2CO_3$ (44 mmol) in acetone (50 mL) was refluxed at 60° C. for 12 h. Upon completion, the solvent was vaporized, and then extracted with DCM/water. Organic layer was combined and concentrated, then purified by column chromatography on silica gel (eluent: hexane/EA, v/v, 20/1 to 10/1), to give the desired product. White solid. Yield 84%. $^{1}$H NMR (400 MHz, chloroform-d) δ 7.65-7.50 (m, 2H), 6.74-6.62 (m, 2H), 4.60 (s, 2H), 3.80 (d, J=0.8 Hz, 3H); $^{13}$C NMR (101 MHz, chloroform-d) δ 169.01, 157.69, 138.42, 117.02, 84.18, 65.27, 52.37.

Example 4—Synthesis of methyl 2-(4-((2-(hydroxymsethyl)pyridin-4-yl) ethynyl)phenoxy)acetate (S5)

Under inert atmosphere, a mixture of 2-(bromomethyl)-4-ethynylpyridine (S3, 5 mmol), methyl 2-(4-iodophenoxy) acetate (S4, 6 mmol), $Pd(PPh_3)_4$ (0.05 mmol), CuI (0.025 mmol), and DIPEA (10 mmol) in THF (30 mL) was heated at 45° C. overnight. Upon completion, the reaction mixture was filtered, concentrated and extracted with DCM/water. The combined organic layer was washed with an EDTA solution, concentrated and purified by column chromatography on silica gel (eluent: hexane/EA, v/v, 3/1 to 1/1), to give the desired product. White solid, Yield 76%. $^{1}$H NMR (400 MHz, chloroform-d) δ 8.47 (d, J=5.1 Hz, 1H), 7.46 (d, J=8.4 Hz, 2H), 7.36 (s, 1H), 7.23 (d, J=5.2 Hz, 1H), 6.88 (d, J=8.4 Hz, 2H), 4.74 (s, 2H), 4.64 (s, 2H), 4.28 (s, 1H), 3.79 (s, 3H); $^{13}$C NMR (101 MHz, chloroform-d) δ 168.92, 159.62, 158.41, 148.47, 133.59, 132.41, 124.07, 122.35, 115.29, 114.80, 93.97, 86.03, 65.13, 64.21, 52.42.

Example 5—Synthesis of 2-azidoethan-1-aminium chloride (S6)

The solution of 2-chloroethan-1-amine (20 mmol) and $NaN_3$ (40 mmol) in water (100 mL) was heated at 80° C. for 12 h. Upon completion, the pH of solution was adjusted to 14 by 1M NaOH. Then, the resultant mixture was extracted by DCM, and the combined organic fractions were dried with $Na_2SO_4$. The solution was filtered, and the filtrate was mixed with equal volume of water, then the pH was adjusted to 1 by 1M HCl and all solvents were evaporated to give a white solid as hydrochloride salt. Yield 65%. $^{1}$H NMR (400 MHz, DMSO-$d_6$) δ 8.38 (s, 3H), 3.68-3.63 (m, 2H), 2.93 (h, J=5.7 Hz, 2H); $^{13}$C NMR (101 MHz, DMSO-$d_6$) δ 47.94, 37.84.

Example 6 Synthesis of N-(2-azidoethyl)-2-(4-((2-(hydroxymethyl)pyridine-4-yl)ethynyl)phenoxy) acetamide (S7)

The solution of methyl-2-(4-((2-(hydroxymethyl)pyridin-4-yl)ethynyl) phenoxy)acetate (S5, 5 mmol) and 2-azido-ethan-1-aminium chloride (S6, 15 mmol) and TEA (30 mmol) in 30 mL THF/MeCN, v/v, 1/1 was heated at 60° C. for 2 d. The reaction was monitored by TLC (eluent: EA). Upon completion, the reaction mixture was concentrated and purified by column chromatography on silica gel (eluent: hexane/EA, v/v, 2/1 to 0/1). White solid. Yield 47%. $^{1}$H NMR (400 MHz, chloroform-d) δ 8.51 (d, J=5.2 Hz, 1H), 7.54-7.48 (m, 2H), 7.39-7.33 (m, 1H), 7.27-7.25 (m, 1H), 6.95-6.83 (m, 3H), 4.75 (s, 2H), 4.52 (s, 2H), 3.91 (s, 1H), 3.50 (s, 4H); $^{13}$C NMR (101 MHz, chloroform-d) δ 168.03, 159.43, 157.63, 148.51, 133.76, 132.23, 124.10, 122.27, 115.85, 114.91, 93.62, 86.26, 67.23, 64.15, 50.73, 38.49.

Example 7—Synthesis of tri-tert-butyl 2,2',2"-(1,4,7,10-tetraazacyclododecane-1,4,7-triyl)triacetate (S8, tBu-DO3A)

To a suspension of cyclen (29 mmol) and sodium acetate (96 mmol) in N,N-dimethylacetamide (DMA, 60 mL) at −18° C. (ice bath with saturated $NH_4C_1$) was added a solution of t-butyl bromoacetate (96 mmol) in DMA (20 mL) dropwise over a period of 30 min. The temperature was maintained at −18° C. during the addition. Then the reaction mixture was allowed to warm to room temperature. After vigorous stirring for 24 h, the reaction mixture was poured into water (300 mL) to give a clear solution. Solid $KHCO_3$ (150 mmol) was added portion wise, and the product precipitated as a white solid. The precipitate was collected by filtration and dissolved in $CHCl_3$ (250 mL). The solution was washed with water (100 mL), dried ($Na_2SO_4$), filtered, and concentrated until only around 20~30 mL. Diethyl ether (250 mL) was added, and the product precipitated as a white fluffy solid. Yield 79%. $^{1}$H NMR (400 MHz, chloroform-d) δ 10.21 (s, 1H), 3.33 (s, 4H), 3.24 (s, 2H), 3.03 (t, J=4.9 Hz, 4H), 2.91-2.79 (m, 12H), 1.41 (s, 18H), 1.40 (s, 9H); $^{13}$C NMR (101 MHz, chloroform-d) δ 170.54, 169.66, 81.76, 81.64, 58.21, 51.28, 49.15, 47.57, 28.23, 28.19.

Example 8—Synthesis of tri-tert-butyl 2,2',2"-(10-((4-((4-(2-((2-azidoethyl) amino)-2-oxoethoxy)phenyl)ethynyl)pyridin-2-yl)methyl)-1,4,7,10-tetraaza-cyclododecane-1,4,7-triyl)triacetate (S9)

To a solution of N-(2-azidoethyl)-2-(4-((2-(hydroxymethyl)pyridin-4-yl)ethynyl) phenoxy)acetamide (S7, 4 mmol) and DIPEA (12 mmol) in DCM (15 mL), MSCl (6 mmol) in DCM (15 mL) was added dropwise. The resulting mixture was stirred at room temperature for 30 min. The reaction was monitored by TLC (eluent: EA). Upon completion, the reacting mixture was concentrated under vacuum. Then the resulting solid was re-dissolved in MeCN (20 mL), followed by adding $K_2CO_3$ (8 mmol) and tBu-$DO_3A$ (S8, 3.6 mmol). The mixture was heated at 50° C. overnight. The reaction can be monitored by ESI-MS until the signal of S8 is no longer detected. Upon completion, the reacting mixture was filtered, and the filtrate was evaporated followed by extraction with DCM/water. The organic layer was combined and concentrated, then purified by column chromatography on silica gel (eluent: DCM/MeOH, v/v, 50/1 to 10/1) to give a white powder. Yield 68%. $^{1}$H NMR (400 MHz, chloroform-d) δ 8.36 (d, J=5.9 Hz, 1H), 8.14 (d, J=5.1

Hz, 1H), 7.41-7.37 (m, 2H), 7.21 (s, 1H), 7.14 (dd, J=5.1, 1.5 Hz, 1H), 6.97-6.93 (m, 2H), 4.60 (s, 2H), 3.48-3.44 (m, 4H), 3.38 (s, 2H), 3.05-2.15 (m, 22H), 1.42 (s, 9H), 1.34 (s, 18H); $^{13}C$ NMR (101 MHz, chloroform-d) δ 172.59, 168.43, 158.69, 158.53, 148.63, 133.53, 132.77, 125.04, 123.85, 115.21, 114.50, 95.04, 85.32, 82.12, 67.06, 58.62, 55.40, 53.50, 50.31, 50.25, 38.33, 27.94, 27.89.

Example 9—General Synthetic Procedure for $Ln-N_3$

The solution of tri-tert-butyl 2,2',2"-(10-((4-((4-(2-((2-azidoethyl)amino)-2-oxoethoxy)phenyl)ethynyl)pyridin-2-yl)methyl)-1,4,7,10-tetraazacyclododecane-1,4,7-triyl)triacetate (S9, 0.05 mmol) in 2 mL TFA/DCM, v/v, 1/1 was stirred for 16 h. Upon completion, the solvent was evaporated, and 0.5 mL MeOH, 0.5 mL de-ionized water, and 0.06 mmol $EuCl_3$·H2O added. The pH of the solution was adjusted to 7-8 by adding 1M NaOH (aq.) and stirred at room temperature for 12 h. The product was then purified by preparative-HPLC. Eu—$N_3$. Pale-yellow powder. Yield 48.5%. Analytical HPLC: Retention time: 12.2 min, Purity: 94.4%. MALDI-TOF HRMS: calc. for $[M-H_2O+H]^+$ 830.2128, found 830.2160. Yb—$N_3$. Pale-yellow powder. Yield 47.9%. Analytical HPLC: Retention time: 12.9 min, Purity: 94.8%. MALDI-TOF HRMS: calc. for $[M-H_2O+H]^+$ 851.2305, found 851.2368.

Example 10—General Synthetic Procedure of LnP19

Under an inert atmosphere, a mixture of $Ln-N_3$ (0.02 mmol), P19 (0.018 mmol), $Cu(CN)_4PF_6$ (0.02 mmol), TBTA (0.02 mmol), DIPEA (0.1 mmol) was stirred at room temperature for 2-4 days, the final product was purified by preparative-HPLC. EuP19. Pale-yellow powder. Yield 34%. Purity 97.2%. Pale-yellow powder. Yield 32.9%. Analytical HPLC: Retention time: 29.4 min, Purity: 96.7%. MALDI-TOF HRMS: calc. for $[M-H_2O+H]$+4288.2600, found 4288.2564. YbP19. Pale-yellow powder. Yield 41%. Purity 96.7%. Pale-yellow powder. Yield 32.9%. Analytical HPLC: Retention time: 28.4 min, Purity: 96.7%. MALDI-TOF HRMS: calc. for $[M-H_2O+H]$+4309.2776, found 4309.2628.

Example 11—Quantum Yield

The quantum yield of EuP19 was measured using relative method to the $EuPhen(TTA)_3$ emission in DMF ($\lambda_{ex}$=360 nm), while that of YbP19 was measured relative to the NIR emission of YbPhen(TTA)3 in toluene ($\lambda_{ex}$=350 nm).

Reagents and Antibodies

P19C and P19 were synthesized in GL Biochem (Shanghai) Ltd. The LMP1 antibody was purchased from Abcam. The antibodies including anti-LMP1 were purchased from Kerafast, while anti-NF-κB p65, anti-NF-κB p105/50, anti-histone H3, anti-GAPDH were purchased from Cell Signaling Technology. Anti-rabbit IgG HRP-linked, anti-mouse IgG HRP-linked, protease/phosphatase inhibitor cocktail were purchased from Cell Signaling Technology. Alexa Fluor 488-conjugated goat anti-mouse IgG, NucBlue fixed cell ready probes (DAPI), and ProLong gold antifade mountant with DAPI were purchased from Invitrogen. The transcriptional response element (TRE)-fluorescent protein reporter, pTRE-EGFP plasmid, was constructed as previously reported.

Cell Line and Culture

LCL3, AG876, AFB1 and C666-1 cells were grown in RPMI-1640 medium. HeLa cells were cultivated in DMEM medium and MRCS cells are cultivated in MEM medium (Gibco, USA). All media are supplemented with 10% fetal bovine serum and 1% penicillin/streptomycin antibiotics. All the cells are cultivated in a humidified incubator with 5% $CO_2$ at 37° C. The pTRE-EGFP plasmid was transduced into LCL3 cells as previously mentioned.

Western Blot Analysis

Cells with different treatments were harvested and washed with phosphate-buffered saline (PBS). Lysis buffer supplied by 1× proteases-phosphatase inhibitor were added into the cells for 5 min on ice. Then the samples were centrifuged at 14,000×g at 4° C. for 20 minutes. The fractionated cell lysates were subjected to SDS-PAGE gel and transferred onto PVDF membranes. Membranes were then blocked by 3% non-fat milk for 30 minutes at room temperature and incubated with specific primary antibodies at 4° C. overnight. They were then washed with TBST buffer and incubated with corresponding secondary antibodies for 1 h at room temperature. Then, the membranes were washed with TBST, and chemiluminescence substrate was added onto the membrane surface. ChemiDoc XRS system and Image Lab Software were used to visualize the blot.

Immunoluminescence Assay

These assays were prepared and conducted at room temperature, unless otherwise stated. Cells with different treatment were fixed by formalin for 15 min. The samples were then washed with PBS and 0.2% Triton-X buffer was added onto the samples for 15 min. 3% BSA in PBS was served as the blocking buffer and applied onto the sample for 30 minutes at room temperature. The primary antibody was diluted in blocking buffer and added onto the sample at 4° C. overnight. The samples were washed with PBS and corresponding secondary antibodies were added over 1 h. Samples were washed with PBS and mountant was applied to each sample. Images were acquired either using a 370 nm laser excitation or from a 370 nm LED excitation of a Nikon Eclipse Ti2 Confocal Microscope. NIR images were captured by a NIRvana TE 640 camera. The signal enhancement of the C666-1 images were obtained by enhancing the exposure of the captured images by the NIS element AR software. Multiphoton microscopy was conducted by Leica TCS SP8 MP System.

In Vivo Inhibition Assays

LCL3 cells were suspended at 1×107 in 200 μL of serum-free medium (RPMI 1640), and then injected into the right flank of female six to eight-week-old NSG mice. When tumors reached an average volume of approximately 400 $mm^3$, intratumor injections were performed twice a week. Tumor bearing mice were randomly divided into three groups, three mice in a group. EuP19, P19C in PBS buffer at the desired dose (25 μg/injection) was injected directly into the tumor. PBS buffer served as the control. All the injections were performed in 100 μL/injection. Body weight and tumor volumes were measured twice per week. Tumor volumes were calculated on the basis of the equation volume $V=(L\times W^2)/2$, where L and W refer to the longer and shorter dimensions respectively. After 16-day treatment, the mice were sacrificed, and their tumors were collected and weighed. Investigators were blind to the treatment groups during the experiments and data analysis. All animal experiments were approved by the Department of Health of the Hong Kong Government and the Hong Kong Baptist University Committee on the Use of Human and Animal Subjects in Teaching and Research.

Computational

The N-terminal region of LMP1 protein was modelled using I-TASSER on-line server (Iterative Threading ASSEmbly Refinement). It was constructed based on the structure of the membrane domain of respiratory protein of *E. coli* (PDB ID: 3RKO), the ovine respiratory complex (PDB ID: 5LNK); the sweet transporter (PDB ID: 5CTG) and NE. Coli YajR transporter (PDB ID: 3WDO). The modelled structured was then checked and agreed with the experimentally defined TM region of LMP1 protein at the N-terminus. P19 and P19C were docked into the modelled N-terminal of LMP1 protein using CABS-dock. The most probable docked conformation of P19 and P19C were selected and used for further analysis.

What is claimed is:

1. A polypeptide comprising SEQ ID NO:1, wherein the N-terminus of the residue at position one of SEQ ID NO:1 is covalently bonded to a moiety represented by the structure; X—Y—Z, wherein X is a click cycloadduct, Y is a lysine residue; and Z is a linker, and each of the residues at positions one, twelve, and twenty of SEQ ID NO:1 is independently a water-soluble residue selected from the group consisting of lysine, arginine, histidine, aspartic acid, and glutamic acid, wherein the click cycloadduct is a moiety of Formula 3:

3

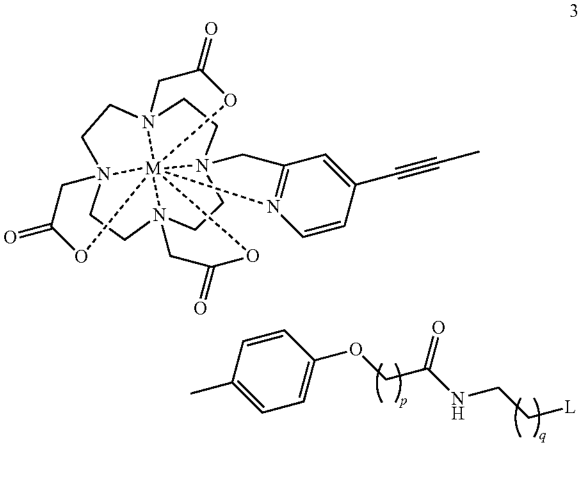

wherein M is a lanthanide or is absent;

p is a whole number selected from 0-6;

q is a whole number selected from 0-6; and

L is a moiety selected from the group consisting of:

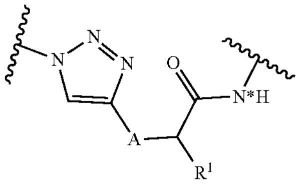

and

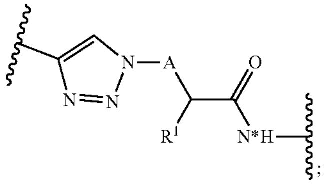

wherein N* is the n-terminal nitrogen of the lysine residue Y;

A is $(CR^2_2)_m$, aryl, or $—CH_2$-aryl;

$R^1$ is hydrogen or amino;

$R^2$ for each instance is independently hydrogen, alkyl, cycloalkyl, or aryl; or two instances of $R^2$ and the carbons to which they are bonded form a 3-6 membered cycloalkyl; and m is a whole number selected from 0-10; and the linker is a moiety of Formula 2:

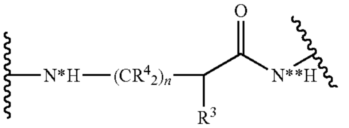

2 wherein N* is covalently bonded to the c-terminal carbon of the lysine residue Y and N** is covalently bonded to the residue at position one of SEQ ID NO:1;

$R^3$ is hydrogen or amino;

$R^4$ for each instance is independently hydrogen, alkyl, cycloalkyl, or aryl; or two instances of $R^4$ and the carbons to which they are bonded form a 3-6 membered cycloalkyl; and n is a whole selected from 0-10.

2. The polypeptide of claim 1, wherein the linker is a moiety selected from the group consisting of:

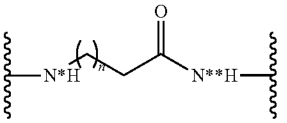

and

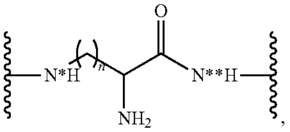

, wherein n is a whole number selected from 0-8.

3. The polypeptide of claim 1, wherein the linker is a moiety having the structure:

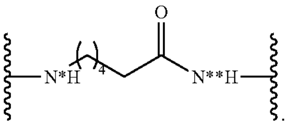

.

4. The polypeptide of claim 1, wherein each of the water-soluble residues is independently selected from the group consisting of lysine, arginine, and histidine.

5. The polypeptide of claim 1, wherein each of the water-soluble residues is lysine.

6. The polypeptide of claim 1, wherein the polypeptide is prepared from a peptide of SEQ ID NO:2.

7. The polypeptide of claim 1, wherein p is 1 or 2; and q is 1, 2, or 3.

8. The polypeptide of claim 1, wherein L is a moiety selected from the group consisting of:

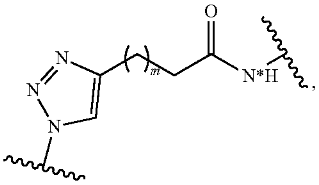

,

-continued

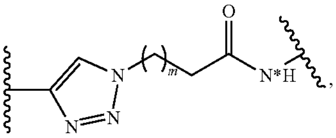

,

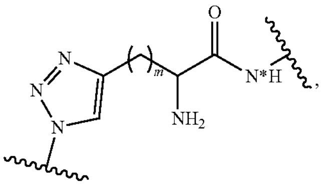

,

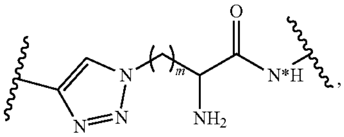

, and

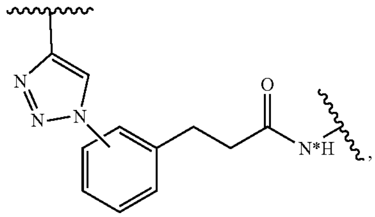

, wherein m is a whole number selected from 1-4.

9. The polypeptide of claim 1, wherein L is a moiety selected from the group consisting of:

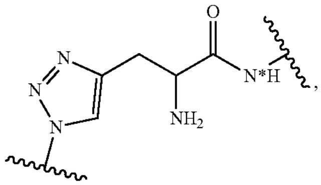

,

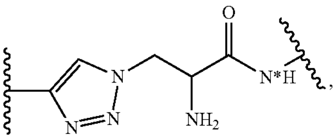

,

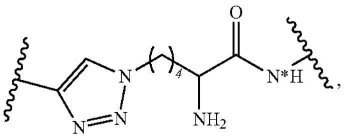

, and

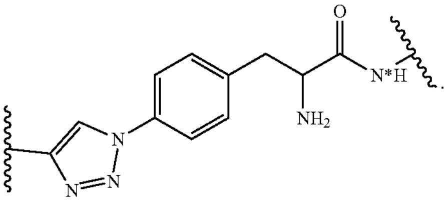

.

-continued

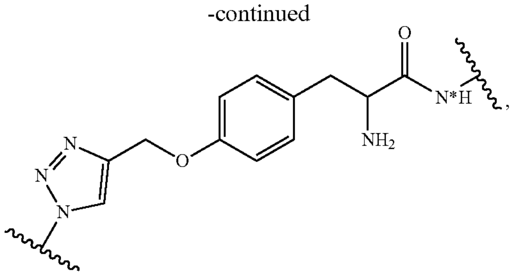

10. The polypeptide of claim 1, wherein L is a moiety selected from the group consisting of:

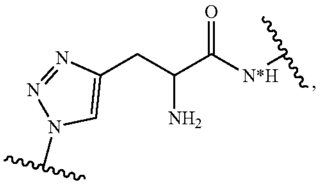

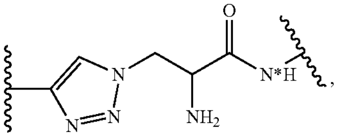

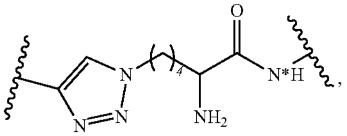

and

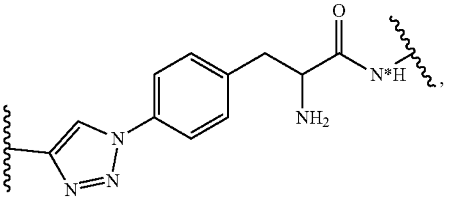

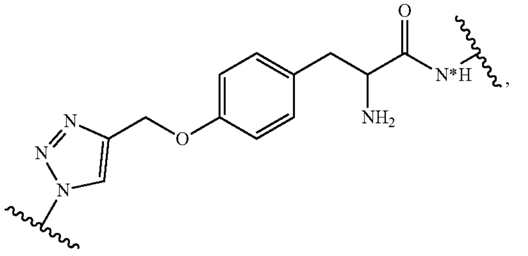

and the linker is a moiety having the structure:

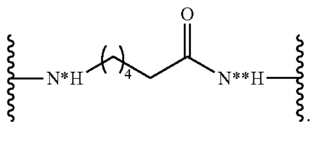

11. The polypeptide of claim 10, wherein each of the water-soluble residues is independently selected from the group consisting of lysine, arginine, and histidine.

12. The polypeptide of claim 1, wherein L is a moiety having the structure:

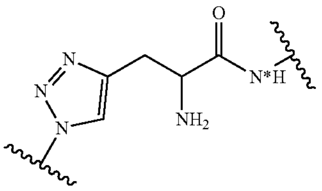

the linker is a moiety having the structure:

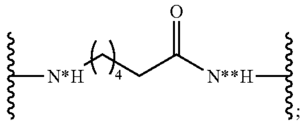

and each of the water-soluble residues is lysine.

13. The polypeptide of claim 12, wherein p is 1; and q is 1.

14. A pharmaceutical composition comprising the polypeptide of claim 1 and at least one pharmaceutically acceptable excipient.

15. A method of treating an Epstein-Barr virus infection in a subject in need thereof comprising administering a therapeutically effective amount of a polypeptide of claim 1 to the subject.

16. A method of treating cancer in a subject in need thereof comprising administering a therapeutically effective amount of a polypeptide of claim 1 to the subject, wherein the cancer is an Epstein-Barr virus-associated cancer.

17. The method of claim 16, wherein the Epstein-Barr virus-associated cancer is selected from the group consisting of Burkitt's lymphoma, non-Hodgkin's lymphoma, Hodgkin's disease, T-cell lymphoma, B-cell lymphoma, B-lymphoproliferative disease, natural killer-cell lymphoma, transplant-associated lymphoproliferative disorders, nasopharyngeal carcinoma, gastric adenocarcinoma, parotid carcinoma, plasmablastic lymphoma, primary effusion lymphoma, and leiomyosarcoma.

18. A method of imaging a cell suspected of being latent membrane protein 1 positive, the method comprising contacting the cell with a polypeptide of claim 1; irradiating the cell with electromagnetic radiation having a wavelength within the activation wavelength of the polypeptide; and imaging the fluorescence of the polypeptide.

* * * * *

SEQUENCE LISTING

```
<160> NUMBER OF SEQ ID NOS: 4

<210> SEQ ID NO 1
<211> LENGTH: 24
<212> TYPE: PRT
<213> ORGANISM: Artificial Sequence
<220> FEATURE:
<223> OTHER INFORMATION: Synthetic Sequence Prepared in the Lab
<220> FEATURE:
<221> NAME/KEY: MISC_FEATURE
<222> LOCATION: (1)..(1)
<223> OTHER INFORMATION: Xaa at position 1 is lysine, arginine,
      histidine, aspartic acid, or glutamic acid
<220> FEATURE:
<221> NAME/KEY: MISC_FEATURE
<222> LOCATION: (12)..(12)
<223> OTHER INFORMATION: Xaa at position 12 is lysine, arginine,
      histidine, aspartic acid, or glutamic acid
<220> FEATURE:
<221> NAME/KEY: MISC_FEATURE
<222> LOCATION: (20)..(20)
<223> OTHER INFORMATION: Xaa at position 20 is lysine, arginine,
      histidine, aspartic acid, or glutamic acid
<220> FEATURE:
<221> NAME/KEY: MISC_FEATURE
<222> LOCATION: (22)..(22)
<223> OTHER INFORMATION: Xaa at position 22 is D-arginine

<400> SEQUENCE: 1

Xaa Leu Asp Leu Ala Leu Lys Phe Trp Leu Tyr Xaa Ile Val Met Ser
1               5                   10                  15

Asp Lys Trp Xaa Arg Xaa Arg Lys
            20


<210> SEQ ID NO 2
<211> LENGTH: 27
<212> TYPE: PRT
<213> ORGANISM: Artificial Sequence
<220> FEATURE:
<223> OTHER INFORMATION: Peptide P19, Synthetic Sequence Prepared in the
      Lab
<220> FEATURE:
<221> NAME/KEY: MISC_FEATURE
<222> LOCATION: (1)..(1)
<223> OTHER INFORMATION: Xaa at Position 1 is D-propargylalanine
<220> FEATURE:
<221> NAME/KEY: MISC_FEATURE
<222> LOCATION: (3)..(3)
<223> OTHER INFORMATION: Xaa at position 3 is 6-aminohexanoic acid
<220> FEATURE:
<221> NAME/KEY: MISC_FEATURE
<222> LOCATION: (25)..(25)
<223> OTHER INFORMATION: Xaa at position 25 is D-arginine

<400> SEQUENCE: 2

Xaa Lys Xaa Lys Leu Asp Leu Ala Leu Lys Phe Trp Leu Tyr Lys Ile
1               5                   10                  15

Val Met Ser Asp Lys Trp Lys Arg Xaa Arg Lys
            20                  25


<210> SEQ ID NO 3
<211> LENGTH: 26
```

-continued

<212> TYPE: PRT
<213> ORGANISM: Artificial Sequence
<220> FEATURE:
<223> OTHER INFORMATION: Peptide P19C, Synthetic Sequence Prepared in
      the Lab
<220> FEATURE:
<221> NAME/KEY: MISC_FEATURE
<222> LOCATION: (2)..(2)
<223> OTHER INFORMATION: Xaa at position 2 is 6-aminohexanoic acid
<220> FEATURE:
<221> NAME/KEY: MISC_FEATURE
<222> LOCATION: (24)..(24)
<223> OTHER INFORMATION: Xaa at position 24 can be any naturally
      occurring amino acid

<400> SEQUENCE: 3

Lys Xaa Lys Leu Asp Leu Ala Leu Lys Ala Ala Ala Ala Lys Ile Val
1               5                   10                  15

Met Ser Asp Lys Trp Lys Arg Xaa Arg Lys
            20                  25

<210> SEQ ID NO 4
<211> LENGTH: 391
<212> TYPE: PRT
<213> ORGANISM: Human herpesvirus 4

<400> SEQUENCE: 4

Glu His Asp Leu Glu Arg Gly Pro Pro Gly Pro Arg Arg Pro Pro Arg
1               5                   10                  15

Arg Pro Pro Leu Ser Ser Ser Leu Gly Leu Ala Leu Leu Leu Leu Leu
            20                  25                  30

Leu Ala Leu Met Phe Trp Leu Tyr Ile Val Met Ser Asp Trp Thr Gly
        35                  40                  45

Gly Ala Leu Leu Val Leu Tyr Ser Phe Ala Leu Met Leu Ile Ile Ile
    50                  55                  60

Ile Leu Ile Ile Phe Ile Phe Arg Arg Asp Leu Leu Cys Pro Leu Gly
65                  70                  75                  80

Ala Leu Cys Leu Leu Leu Leu Met Ile Thr Leu Leu Leu Ile Ala Leu
                85                  90                  95

Trp Asn Leu Arg Gly Gln Ala Leu Tyr Leu Gly Ile Val Leu Phe Ile
            100                 105                 110

Phe Gly Cys Leu Leu Val Leu Gly Leu Trp Ile Tyr Leu Leu Glu Ile
        115                 120                 125

Leu Trp Arg Leu Gly Ala Thr Ile Trp Gln Leu Leu Ala Phe Phe Leu
    130                 135                 140

Ala Phe Phe Leu Asp Leu Ile Leu Leu Ile Ile Ala Leu Tyr Leu Gln
145                 150                 155                 160

Gln Asn Trp Trp Thr Leu Leu Val Asp Leu Leu Trp Leu Leu Leu Phe
                165                 170                 175

Leu Ala Ile Leu Ile Trp Met Tyr Tyr His Gly Gln Arg His Ser Asp
            180                 185                 190

-continued

```
Glu His His His Asp Asp Ser Leu Pro His Pro Gln Gln Ala Thr Asp
        195                 200                 205

Asp Ser Ser His Glu Ser Asp Ser Asn Ser Asn Glu Gly Arg His His
    210                 215                 220

Leu Leu Val Thr Gly Ala Gly Asp Gly Pro Pro Leu Cys Ser Gln Asn
225                 230                 235                 240

Leu Gly Ala Pro Gly Gly Gly Pro Asp Asn Gly Pro Gln Asp Pro Asp
                245                 250                 255

Asn Thr Asp Asp Asn Gly Pro Gln Asp Pro Asp Asn Thr Asp Asp Asn
            260                 265                 270

Gly Pro Gln Asp Pro Asp Asn Thr Asp Asp Asn Gly Pro Gln Gly Pro
        275                 280                 285

Asp Asn Thr Asp Asp Asn Gly Pro Gln Gly Pro Asp Asn Thr Asp Asp
    290                 295                 300

Asn Gly Pro His Asp Pro Leu Pro His Asn Pro Ser Asp Ser Ala Gly
305                 310                 315                 320

Asn Asp Gly Gly Pro Pro Glu Leu Thr Glu Glu Val Glu Asn Lys Gly
                325                 330                 335

Gly Asp Arg Gly Pro Pro Ser Met Thr Asp Gly Gly Gly Gly His Ser
            340                 345                 350

His Asp Ser Gly Arg Gly Gly Gly Asp Pro His Leu Pro Thr Leu Leu
        355                 360                 365

Leu Gly Thr Ser Gly Ser Gly Gly Asp Asp Asp Asp Pro His Gly Pro
    370                 375                 380

Val Gln Leu Ser Tyr Tyr Asp
385                 390
```